(12) United States Patent
Svanborg et al.

(10) Patent No.: US 11,865,161 B2
(45) Date of Patent: *Jan. 9, 2024

(54) PROPHYLACTIC AND NUTRACEUTICAL THERAPY

(71) Applicant: HAMLET PHARMA AB, Lund (SE)

(72) Inventors: Catharina Svanborg, Malmo (SE); Manoj Puthia, Lund (SE); Chin Shing Ho, Lund (SE)

(73) Assignee: Hamlet Pharma AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/389,451

(22) Filed: Apr. 19, 2019

(65) Prior Publication Data

US 2019/0282669 A1   Sep. 19, 2019

Related U.S. Application Data

(62) Division of application No. 14/419,519, filed as application No. PCT/GB2013/052132 on Aug. 8, 2013, now Pat. No. 11,103,561.

(30) Foreign Application Priority Data

Aug. 9, 2012 (GB) ....................... 1214234
Aug. 9, 2012 (GB) ....................... 1214237

(51) Int. Cl.

| A61K 38/38 | (2006.01) |
|---|---|
| A61K 31/201 | (2006.01) |
| A61K 35/20 | (2006.01) |
| A23L 33/18 | (2016.01) |
| A61P 35/00 | (2006.01) |
| A61K 9/00 | (2006.01) |
| A61K 47/12 | (2006.01) |

(52) U.S. Cl.
CPC ............. *A61K 38/38* (2013.01); *A23L 33/18* (2016.08); *A61K 9/0095* (2013.01); *A61K 31/201* (2013.01); *A61K 35/20* (2013.01); *A61K 47/12* (2013.01); *A61P 35/00* (2018.01)

(58) Field of Classification Search
None
See application file for complete search history.

(56) References Cited

U.S. PATENT DOCUMENTS

| 2010/0092497 A1 | 4/2010 | Kanwar et al. |
| 2011/0177224 A1 | 7/2011 | Perlman |

FOREIGN PATENT DOCUMENTS

| WO | 96/04929 A1 | 2/1996 |
| WO | 99/26979 A1 | 6/1999 |
| WO | 03/074547 A2 | 9/2003 |
| WO | 2005/082406 A1 | 9/2005 |
| WO | 2008/058547 A2 | 5/2008 |
| WO | 2008/138348 A1 | 11/2008 |
| WO | 2009/012784 A2 | 1/2009 |
| WO | 2010/079362 A1 | 7/2010 |
| WO | 2010/131237 A1 | 11/2010 |
| WO | 2012/069836 A2 | 5/2012 |
| WO | WO2012-069836 | * 5/2012 |
| WO | 2014/023976 A1 | 2/2014 |

OTHER PUBLICATIONS

The National Cancer Institute (<https://www.cancer.gov/types> accessed Apr. 13, 2020).*
Zeineldin et al. ("More than two decades of APC modeling in rodents" Biochim Biophys Acta. Aug. 2013;1836(1); 80-89).*
National Cancer Institute (<Definition of gastrointestinal tract—NCI Dictionary of Cancer Terms—National Cancer Institute> accessed Dec. 17, 2020).*
Merck Manual teaches Familial Adenomatous Polyposis (https://www.merckmanuals.com/professional/gastrointestinal-disorders/tumors-of-the-gastrointestinal-tract/familial-adenomatous-polyposis accessed Dec. 3, 2020).*
Merck manual https://www.merckmanuals.com/home/digestive-disorders/tumors-of-the-digestive-system/stomach-cancer> accessed Dec. 17, 2020).*
https://www.cancer.org/cancer/stomach-cancer/causes-risks-prevention/risk-factors.html, accessed Sep. 24, 2021.*
Mossberg et al. ("HAMLET treatment delays bladder cancer development" Investigative Urology; vol. 183, 1590-1597, Apr. 2010).*
Storm et al. ("The mechanism of HAMLET induced cell death-cellular signaling, oncogenesis and clinical perspectives" Jun. 2012: Thesis Lund University.*
Aits et al., "HAMLET (human a-lactalbumin made lethal to tumor cells) triggers autophagic tumor cell death," Int. J. Cancer, 2009, pp. 1008-1019, vol. 124.
Bienz et al., "Linking Colorectal Cancer to Wnt Signaling," Cell, 2000, pp. 311-320, vol. 103.
Extended European Search Report from related European Application No. 17187031.4, dated Jan. 26, 2018; 9 pgs.
Fang et al., "Influence of pH on the Structure and Oleic Acid Binding Ability of Bovine a-Lactalbumin," Journal of Protein Chemistry, 2012, pp. 564-572, vol. 31.
Great Britain Search Report, Application No. GB1214234.5, dated Dec. 11, 2012; 5 pgs.
Ilyas et al., "ß-Catenin mutations in cell lines established from human colorectal cancers," PNAS, 1997, pp. 10330-10334, vol. 94.
International Search Report and Written Opinion from related International Application No. PCT/GB2013/052132, dated Dec. 9, 2013; 13 pgs.

(Continued)

*Primary Examiner* — Julie H Alstrum-Acevedo
*Assistant Examiner* — Tara L Martinez
(74) *Attorney, Agent, or Firm* — Polsinelli, PC

(57) ABSTRACT

A biologically active complex comprising a polypeptide having the sequence of a naturally occurring protein or a variant thereof, wherein said polypeptide is at least partially unfolded as compared to the said naturally occurring protein for example as a result of a modification of at least one cysteine residue; or a peptide of up to 50 amino acids; and a fatty acid or lipid or a salt thereof, for use in prophylactic treatment of cancers, in particular of the gastrointestinal tract. Compositions that may comprise the complex and have use as nutraceuticals are obtainable from milk or milk fractions and form a further aspect of the invention.
Methods of treatment in particular for the prevention of cancer form a further aspect of the invention.

11 Claims, 26 Drawing Sheets

Specification includes a Sequence Listing.

(56) References Cited

OTHER PUBLICATIONS

Kamijima et al., "Heat-treatment method for producing fatty acid-bound alpha-lactalbumin that induces tumor cell death," Biochemical and Biophysical Research Communications, 2008, pp. 211-214, vol. 376, No. 1.
Knyazeva et al., "Who Is Mr. Hamlet? Interaction of Human a-Lactalbumin with Monomeric Oleic Acid," Biochemistry, 2008, pp. 13127-13137, vol. 47, No. 49.
Liskova et al., "Cytotoxic complexes of sodium oleate with ß-lactoglobulin," Eur. J. Lipid Sci. Technol., 2011, pp. 1207-1218, vol. 113.
Min et al., "Alternatively folded proteins with unexpected beneficial functions," Biochemical Society Transactions, 2012, pp. 746-751, vol. 40.
Moser et al., "A Dominant Mutation That Predisposes to Multiple Intestinal Neoplasia in the Mouse," Science, 1990, pp. 322-324, vol. 247.
Mossberg et al., "Structure and function of human a-lactalbumin made lethal to tumor cells (HAMLET)-type complexes," FEBS Journal, 2010, pp. 4614-4625, vol. 277, No. 22.
Mossberg et al., "HAMLET Treatment Delays Bladder Cancer Development," The Journal of Urology, 2010, pp. 1590-1597, vol. 183.
Pettersson-Kastberg et al., "a-Lactalbumin, Engineered to be Non-native and Inactive, Kills Tumor Cells when in Complex with Oleic Acid: A New Biological Function Resulting from Partial Unfolding," J. Mol. Biol., 2009, pp. 994-1010, vol. 394.
Rammer et al., "BAMLET Activates a Lysosomal Cell Death Program in Cancer Cells," Molecular Cancer Therapeutics, 2010, pp. 24-32, vol. 9, No. 1.
Rosner et al., "The Human a-Lactalbumin Molten Globule: Comparison of Structural Preferences at pH 2 and pH 7," J Mol Biol., 2009, pp. 351-362, vol. 394, No. 2-3.
Storm et al., "Conserved features of cancer cells define their sensitivity to HAMLET-induced death; c-Myc and glycolysis," Oncogene, 2011, pp. 4765-4779, vol. 30, No. 48.
Storm et al., "A Unifying Mechanism for Cancer Cell Death through Ion Channel Activation by Hamlet," PLoS One, 2013, e58578, pp. 1-18, vol. 8, No. 3.
Subramanian et al., "Gene set enrichment analysis: A knowledge-based approach for interpreting genome-wide expression profiles," PNAS, 2005, pp. 15545-15550, vol. 102, No. 43.
Svanborg et al., "HAMLET Kills Tumor Cells by an Apoptosis-Like Mechanism—Cellular, Molecular, and Therapeutic Aspects," Advances in Cancer Research, 2003, pp. 1-29, vol. 88.
Svensson et al., "Conversion of a-lactalbumin to a protein inducing apoptosis," PNAS, 2000, pp. 4221-4226, vol. 97, No. 8.
Vogelstein et al., "Genetic Alterations During Colorectal-Tumor Development," The New England Journal of Medicine, 1988, pp. 525-532, vol. 319, No. 9.
Watanabe et al., "Identification of Canine a-Lactalbumin," J. Vet. Med. Sci., 2000, pp. 1217-1219, vol. 62, No. 11.
Wilhelm et al., "Protein oligomerization induced by oleic acid at the solid-liquid interface—equine lysozyme cytotoxic complexes," FEBS Journal, 2009, pp. 3975-3989, vol. 276.
Zhang et al., "Cytotoxic aggregates of a-lactalbumin induced by unsaturated fatty acid induce apoptosis in tumor cells," Chemico-Biological Interactions, 2009, pp. 131-142, vol. 180.
Zunszain et al., "Crystal structural analysis of human serum albumin complexed with hemin and fatty acid," BMC Structural Biology, 2003, 9 pgs., vol. 3, No. 6.
"The Effect of a Change in pH on the Activity of Enzymes," Boredofstudies.org (<https://boredofstudies.org/threads/the-effect-of-a-change-in-ph-on-the-activity of-enzymes.242574/> available online Mar. 25, 2010), printed Sep. 29, 2019, pp. 1-13.
E. Conis, "Poring over facts about milk: cow's, goat's, soy, almond, rice and hemp," Chicago Tribune, Oct. 19, 2009, (<https://www.chicagotribune.com/lifestyles/sns-green-substitutes-for-milk-story.html), 13 pgs.
C. Shih, "Don't Have a Cow! Here's How to Pick the Best Milk for You," Jan. 21, 2014, retrieved on Sep. 29, 2019, (<https://greatist.com/health/cows-milk-benefits-comparison#1> 2014), 13 pgs.
Huhtanen et al., "Factors Which Increase Acid Production in Milk by Lactobacilli," Appl. Microbiol., 1963, pp. 20-22, vol. 11.
Nigel Slater's yogurt recipes/Food/The Guardian, (<https://www.theguardian.com/lifeandstyle/2010/apr/25/nigel-slater-yogurt-recipes> Apr. 24, 2010), retrieved Apr. 12, 2020, 6 pgs.
Cornell University, New York State Agricultural Experiment Station, (Yogurt Production: Fact Sheets for the Small Scale Food Entrepreneur Jan. 2007), 3 pgs.
CalorieKing, "Calories in Whole Milk Powder," (<https://www.calorieking.com/us/en/foods/f/calories-in-other-milk-products-whole-milk-powder/umLMnLXnQAKIN3d1zmzbBg>accessed Apr. 12, 2020), 8 pgs.
Schmidt, "Effect of acidulant addition on yogurt fermentation," Kansas Agricultural Experiment Station Research Reports (vol. 0, Issue 2, Dairy Research, 2009), 6 pgs.
"Hydrochloric Acid," ERCO Worldwide <https://www.ercoworldwide.com/index.php/products/hydrochloric-acid/> Jun. 27, 2012).
Office Action from related U.S. Appl. No. 14/419,519, dated Oct. 11, 2019; 11 pgs.
Office Action from related U.S. Appl. No. 14/419,519, dated May 13, 2020; 18 pgs.

\* cited by examiner

Control | HAMLET treated

Control | HAMLET treated

Fig. 3A

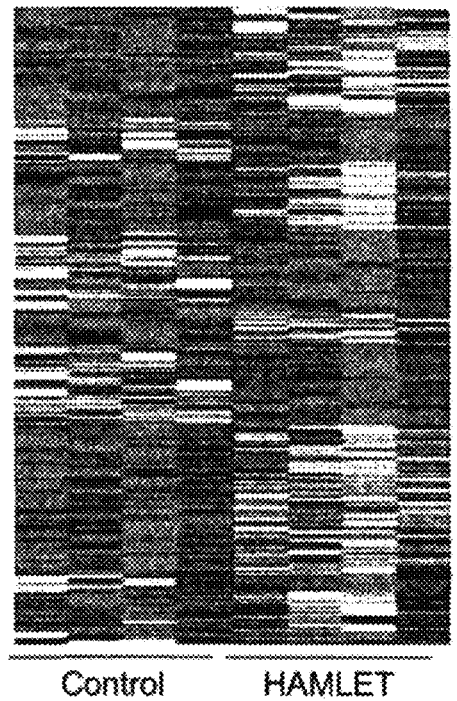

Fig. 3B

Gene Set Enrichment Analysis

| Gene set | FDR q-val |
|---|---|
| KEGG Retinol Metabolism | 0.017 |
| WNT Signalling | 0.032 |
| KEGG Hedgehog Signalling Pathway | 0.05 |
| KEGG ECM Receptor Interaction | 0.05 |
| KEGG Glycolysis/Glyconegenesis | 0.05 |
| KEGG Glutathione Metabolism | 0.043 |

Ingenuity Pathway Analysis

| Canonical Pathway | -log(p-value) |
|---|---|
| Glycocolysis/Gluconeogenesis | 9.36 |
| Fructose and Mannose Metabolism | 6.05 |
| Metabolism of Xenobiotics by Cytochrome P450 | 5.78 |
| LPS/IL-1 Mediated Inhibition of RXR Function | 5.46 |
| Arachidonic Acid Metabolism | 5.17 |
| Fatty Acid Metabolism | 4.71 |

Control — HAMLET treated

PROPHYLACTIC AND NUTRACEUTICAL THERAPY

CROSS-REFERENCE TO RELATED APPLICATIONS

The application is a divisional application of U.S. patent application Ser. No. 14/419,519, filed Feb. 4, 2015, which is a National Stage Entry of PCT/GB2013/052132, filed Aug. 8, 2013, which claims priority to GB Application No. 1214234.5, filed Aug. 9, 2012, and GB Application No. 1214237.8, filed Aug. 9, 2012, the disclosure of each is hereby incorporated by reference in its entirety.

SEQUENCE LISTING

This application contains a Sequence Listing that has been submitted in ASCII format via EFS-Web and is hereby incorporated by reference in its entirety. The ASCII copy, created on Oct. 21, 2013, is named Seq_Listing.txt, and is about 5000 bytes in size.

DETAILED DESCRIPTION

The present invention relates to prophylactic therapy in particular for the prevention of cancer of the gastrointestinal tract and in particular colon cancer. Treatments may be effected using a nutraceutical regime and novel nutraceutical compositions are also described and claimed. These compositions may be used in particular for the prevention but also for the therapeutic treatment of proliferative disease such as cancer, as well as having antibacterial and antiviral applications. Methods for preparing these compositions and their use in therapy including prophylaxis and as nutraceuticals form further aspects of the invention.

Colon cancers remain a major therapeutic challenge and colon cancer is one of the leading causes of cancer-related death. While the 5-year survival rate is extremely favorable after early detection and treatment of localized tumors, most colorectal cancers are either locally or distantly invasive at the time of diagnosis, limiting treatment options and lowering survival. More than 80% of all sporadic and hereditary colorectal tumors show a loss of APC (adenomatous polyposis *coli*) function, often due to truncating mutations in the gene (Vogelstein, et al. (1988) N Engl J Med 319: 525-532). APC acts as a tumor suppressor by operating as a scaffold protein together with Axin for casein kinase 1 (CK1) and glycogen synthase kinase 3 (GSK3), which phosphorylate β-catenin for subsequent ubiquitination and proteasomal degradation. Tumor formation is initiated by a second, somatic mutation of the wild-type APC allele, which stimulates β-catenin-dependent gene expression, including genes like Cyclin DL VEGF and Cox-2 (Bienz M et al. (2000) Cell 103: 311-320). With time, the tumors accumulate additional mutations, affecting for example KRAS and apoptotic genes like p53 (Vogelstein et al supra.). The APC point mutation is sufficient for tumor initiation however, and mice carrying the $Apc^{Min/+}$ allele with a nonsense point mutation at nucleotide 2549 spontaneously develop multiple intestinal adenomas and have therefore been extensively used as a model of familial adenomatous polyposis *coli* and human colorectal cancer (Moser A R et al (1990) Science 247: 322-324).

HAMLET (human alpha-lactalbumin made lethal to tumor cells) is the first member of a new family of tumoricidal unfolded protein-lipid complexes, consisting of partially unfolded α-lactalbumin and oleic acid. Initially isolated in the form of a fraction obtained by passing a casein containing fraction of human milk down an ion exchange column under high salt conditions (WO96/004929), it was found to be biologically active and in particular had an antibacterial activity. Subsequently, other methods for preparing active complexes have been derived including methods in which α-lactalbumin from various sources and oleic acid are heated together in solution. In addition however, HAMLET and related complexes such as BAMLET, derived from bovine alpha-lactalbumin, has been found to kill transformed cells such as tumour cells or papilloma cells, as well as having antiviral activity. HAMLET kills many types of tumor cells in vitro and this tumoricidal activity is maintained in vivo, as shown in animal models of human glioblastoma xenografts and bladder cancer as well as in clinical studies. Topical application of HAMLET removed or reduced skin papillomas and local instillations of HAMLET killed bladder cancer cells but not healthy cells in surrounding tissues and caused a reduction in tumor size. The sensitivity of tumor cells to HAMLET reflects oncogenic transformation and is modified by the glycolytic state of the cell (Storm P, et al. (2011). Oncogene). shRNA silencing of c-Myc or Ras pathway members conferred resistance to HAMLET and the level of c-Myc expression paralleled HAMLET sensitivity. Furthermore, glucose deprivation sensitized tumor cells to HAMLET and the HAMLET-sensitivity was modified by shRNAs targeting glycolytic enzymes. Additionally, HAMLET was shown to have pronounced effects on global metabolism with a rapid metabolic paralysis in tumor cells and potential diversion of the glycolytic flux towards the pentose phosphate pathway.

Addressing if HAMLET or the related therapeutic entities may be used for colon cancer therapy was considered by the applicants. The constituents of HAMLET are present in human milk, where the complex is formed after unfolding of the protein and hydrolysis of oleic acid from milk triglycerides. At low pH, HAMLET may be assembled, for passage through the gastrointestinal tract of the breast-fed child. In vitro studies have shown that HAMLET is protease resistant, suggesting that by surviving the harsh gastrointestinal environment HAMLET may reach and kill cells that are sensitive to its effects, including colon cancer progenitors. The applicants investigated if HAMLET acts as a colon cancer therapeutic, using peroral administration in the $APC^{min}$ mouse model.

In view of the step-wise tumor development, taking place in this model, the applicants also explored if HAMLET acts prophylactically in genetically susceptible mice. The results clearly demonstrate prophylactic as well as therapeutic effects of HAMLET, as well as targets in the Wnt/β-catenin signaling pathway.

Whilst the use of complexes such as HAMLET have been demonstrated previously as being therapeutic in the treatment of a range of pre-existing cancers including mucosal cancers (WO2005/082406), and for the prophylactic treatment of bacterial infection, it has not been shown previously that it is useful in the prevention of cancer. Thus this finding opens up a new approach to the prophylaxis of proliferative disease.

According to a first aspect of the present invention there is provided a biologically active complex comprising a polypeptide having the sequence of a naturally occurring protein or a variant thereof, wherein said polypeptide is at least partially unfolded as compared to the said naturally occurring protein for example as a result of a modification of at least one cysteine residue; or a peptide of up to 50 amino acids; and a fatty acid or lipid or a salt thereof, for use in prophylactic treatment of cancers, in particular of the gastrointestinal tract.

This discovery means that the complexes can be used in the prevention of cancers and in particular colon cancer. It may be used in any individual but may find particular utility in individuals who have a genetic predisposition to colon cancer, in particular as a result of mutation such as a truncation of the APC gene.

The complex may be administered either in the form of a pharmaceutical, in which case the complex is provided in combination with a pharmaceutically acceptable carrier, or alternatively, the complex may be combined with a foodstuff, such as a dairy product such as yoghurt for use as a nutraceutical. Compositions of this type form a further aspect of the invention.

The complex or composition containing it is suitably administered orally so that it may directly access the gastrointestinal tract.

In a particular embodiment, the polypeptide present in the complex may have the sequence of an α-lactalbumin or a variant thereof or a lysozyme or a variant thereof.

As used herein, the term "biologically active" means that the complex has a biological activity, which is different from—or stronger than the individual components. In particular, the complex is able to induce cell death in particular selectively in tumour cells and/or has a bactericidal or antiviral effect not seen with the native protein including for example monomeric α-lactalbumin forms, although other therapeutic effects may be available.

Suitable peptides for use in the complex of the invention may be a fragment of the polypeptide or of the naturally occurring protein. The term "fragment" as used herein refers to any portion of the given amino acid sequence which will form a complex with the similar activity to complexes including the complete protein sequence such as an α-lactalbumin or lysozyme amino acid sequence. Fragments may comprise more than one portion from within the full-length protein, joined together. Portions will suitably comprise at least 5 and preferably at least 10 consecutive amino acids from the basic sequence.

Suitable fragments will include deletion mutants comprising at least 10 amino acids, for instance at least 20, more suitably at least 50 amino acids in length or analogous synthetic peptides with similar structures. They include small regions from the protein or combinations of these.

In a particular embodiment, there is provided a biologically active complex comprising a peptide of no more than 50 amino acids, and a pharmaceutically acceptable salt of a fatty acid or lipid.

The peptide has no more than 50 amino acids, and in particular may have from 10-45 amino acids. Such complexes are easier to prepare and the starting materials are less costly. For instance, peptides may be prepared using conventional methods for the production of peptides. The complexes formed may be easier to handle and formulate for administration, due to the smaller molecular weight.

Any peptide is suitably derived from a naturally occurring protein or a variant thereof. Suitable proteins are those identified as being active in such complexes, such as alpha-lactalbumin, beta-lactoglobulin or lysozyme. In particular, the peptide is a fragment of alpha-lactalbumin and specifically a fragment of the alpha domain of alpha-lactalbumin. In a particular embodiment, the peptide comprises amino acids of the Alpha 1 (residues 1-40) or Alpha 2 (residues 81-123) of human alpha-lactalbumin, or analogous regions of other alphalactalbumins such as bovine alpha-lactalbumin.

The peptide suitably contains no elements that give rise to folding and therefore suitably lacks amino acids that give rise to intramolecular bonding such as cysteine residues. In particular, where the peptide is derived from a naturally occurring protein, any cysteine residues are replaced by other amino acids such as alanine.

Thus in a particular embodiment, the complex comprises amino acids of the Alpha 1 (residues 1-40) or Alpha 2 (residues 81-123) of human alpha-lactalbumin wherein the cysteines are replaced with other amino acids such as alanine, to prevent any intra-molecular bonding.

Thus the peptide may be of SEQ ID NO 3 or SEQ ID NO 4

```
                                          (SEQ ID NO 3)
    KQFTKXELSQLLKDIDGYGGIALPELIXTMFHTSGYDTQA (SEQ ID NO 4)
    LDDDITDDIMXAKKILDIKGIDYWLAHKALXTEKLEQWLXEKL
``` where X is an amino acid residue other than cysteine.

A particular example of such sequences are those of SEQ ID NO 5 or SEQ ID NO 6.

```
                                          (SEQ ID NO 5)
    KQFTKAELSQLLKDIDGYGGIALPELIATMFHTSGYDTQA (SEQ ID NO 6)
    LDDDITDDIMAAKKILDIKGIDYWLAHKALATEKLEQWLAEKL.
```

Other peptides may also be used in the complex and the suitability may be tested by determining whether complexes with a fatty acid salt are active, for instance in opening potassium ion channels and/or killing cells using methods as described hereinafter.

For instance, suitable fragments of α-lactalbumin are those described above which are derived solely from the alpha domains, but others that may be selected include the region, which forms the alpha or the beta domains or the interface between the alpha and the beta domains, in human α-lactalbumin, defined by amino acids 34-38 and 82-86 in the structure. Thus suitable fragments will include these regions, and preferably the entire region from amino acid 40-105 of the native protein. However, other active fragments may be found.

The expression "variant" refers to proteins or polypeptides having a similar biological function but in which the amino acid sequence differs from the base sequence from which it is derived in that one or more amino acids within the sequence are substituted for other amino acids. Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:

| Class | Amino acid examples |
| --- | --- |
| Nonpolar: | A, V, L, I, P, M, F, W |
| Uncharged polar: | G, S, T, C, Y, N, Q |

| Class | Amino acid examples |
|---|---|
| Acidic: | D, E |
| Basic: | K, R, H. |

As is well known to those skilled in the art, altering the primary structure of a peptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptide's conformation.

Non-conservative substitutions are possible provided that these do not interrupt the function of the DNA binding domain polypeptides. Broadly speaking, fewer non-conservative substitutions will be possible without altering the biological activity of the polypeptides.

Determination of the effect of any substitution (and, indeed, of any amino acid deletion or insertion) is wholly within the routine capabilities of the skilled person, who can readily determine whether a variant polypeptide retains the fundamental properties and activity of the basic protein. For example, when determining whether a variant of the polypeptide falls within the scope of the invention, the skilled person will determine whether complexes comprising the variant retain biological activity (e.g. tumour cell death) of complexes formed with unfolded forms of the native protein and the polypeptide has at least 60%, preferably at least 70%, more preferably at least 80%, yet more preferably 90%, 95%, 96%, 97%, 98%, 99% or 100% of the native protein.

Variants of the polypeptide may comprise or consist essentially of an amino acid sequence with at least 70% identity, for example at least 75%, 80%, 85%, 90%, 91%, 92%, 93%, 94%, 96%, 97%, 98% or 99% identity to a native protein sequence such as an alphalactalbumin or lysozyme sequence.

The level of sequence identity is suitably determined using the BLASTP computer program with the native protein sequences as the base sequence. This means that native protein sequences form the sequence against which the percentage identity is determined. The BLAST software is publicly available at http://blast.ncbi.nlm.nih.gov/Blast.cgi (accessible on 12 Mar. 2009).

The protein may comprise lysozyme and in particular equine lysozyme.

However, in a particular embodiment, the polypeptide is an α-lactalbumin such as human, bovine or ovine α-lactalbumin. Whilst variants of these as described above may be useful in the invention, for nutraceutical use in particular, it may be preferable to utilize the native proteins in the products. A particular embodiment used human α-lactalbumin. In another embodiment, the α-lactalbumin is bovine α-lactalbumin. The sequence of a wide range of α-lactalbumins is known in the literature, for example as shown in Watanabe et al., J. Vet Med Sci, (2000) 62(11); 1217-1219, the content of which is incorporated herein by reference.

In another embodiment, the polypeptide comprises a recombinant protein having the sequence of α-lactalbumin or a fragment thereof but which lacks intra-molecular disulfide bonds or cross-links. By ensuring that the recombinant protein lacks intra-molecular disulfide crosslinks, the molecule will be three-dimensionally non-native and completely inactive in terms of its original endogenous biological activity. This may be achieved for example by changing cysteine residues in the native α-lactalbumin to other residues, in particular alanine residues, although other means, for example by adding thiol compounds, or altering the pH of the protein may be considered. Preferably all cysteine residues will be changed to other residues, such as alanine residues. In particular the recombinant protein is based upon the sequence of human α-lactalbumin but α-lactalbumin from other sources, including bovine or ovine α-lactalbumin may be used to derive the recombinant protein.

In a particular embodiment, the polypeptide is a recombinant protein having the sequence of native mature α-lactalbumin but which has all of the cysteines found at positions 6, 28, 61, 73, 77, 91, 111 and 120 in the full length sequence of mature human α-lactalbumin mutated to other amino acids, such as alanine, which do not give rise to disulphide bridges. Thus a particular of a protein that may be utilised in accordance with the invention comprises a protein of SEQ ID NO 1.

(SEQ ID NO 1)
KQFTKAELSQLLKDIDGYGGIALPELIATMFHTSGYDTQAIVENNESTE

YGLFQISNKLWAKSSQVPQSRNIADISADKFLDDDITDDIMAAKKILDI

KGIDYWLAHKALATEKLEQWLAEKL where the bold type indicates positions of mutations of cysteines in native human α-lactalbumin.

As reported in WO2010079362, additional amino acid residues, for example up to 20 amino acids, may be attached at N and/or C terminal of the protein, if convenient, for example for expression purposes. Thus in particular, a recombinant protein as shown in SEQ ID NO. 1 but with an additional methionine at the N-terminus (SEQ ID NO 2 shown below) has been used in the method of the invention.

(SEQ ID NO 2)
MKQFTKAELSQLLKDIDGYGGIALPELIATMFHTSGYDTQAIVENNEST

EYGLFQISNKLWAKSSQVPQSRNIADISADKFLDDDITDDIMAAKKILD

IKGIDYWLAHKALATEKLEQWLAEKL

The polypeptide used in the complex is suitably in pure form, and is suitably prepared using conventional methods of peptide synthesis or by recombinant expression. In particular, DNA encoding the required recombinant α-lactalbumin can be inserted into suitable expression vectors such as plasmids, which can then be employed to transform host cells, for example, prokaryotic cells such as E. coli or eukaryotic cells such as particular insect cells using conventional methods.

Suitably fatty acids or lipids include those known to provide biologically active complexes. These include fatty acids, for example as described in WO2008058547. Where salts are used, these are suitably water soluble salt. Particular examples of suitable salts may include alkali or alkaline earth metal salts. In a particular embodiment, the salt is an alkali metal salt such as a sodium- or potassium salt. Where used in pharmaceuticals, the salts will be pharmaceutically acceptable, and will be suitable for food use when used in nutraceuticals.

Particular examples of fatty acids or lipids used in the present invention are those having from 4-30, for example from 6 to 28, such as from 8 to 26 carbon atoms. In particular embodiments, the fatty acid or lipid has from 10 to 24, such as from 12 to 22, for example from 14 to 20 carbon atoms. In particular, the fatty acid or lipid will have 16, 17, 18 or 20 carbon atoms. The fatty acids may be saturated or unsaturated.

In particular however, the complexes of the invention utilize salts of acids having 18 carbon atoms. A specific example is a salt of oleic acid, an in particular a salt of C18:1 oleic acid of formula $CH_3(CH_2)_7CH\!=\!CH(CH_2)_7COOH$ or $CH_3(CH_2)_7CH\!=\!CH(CH_2)_7COO^-$.

The complex may be prepared using methods similar to those described for example in WO99/26979, WO2008/138348 and WO2010/131237 the content of which is incorporated herein by reference. Not only has it been found that complexes can be prepared by contacting unfolded α-lactalbumin or derivatives thereof with co-factors in particular oleic acid or salts thereof under ion exchange conditions such as those found on an ion exchange column, but also incubation of solutions of α-lactalbumin or derivatives thereof with a co-factor at elevated temperatures, for example of from 50-80° C., for example from 50-70° C. and in particular between 55-60° C. will result in the production of suitable complexes for use in the invention.

These methods however have generally focused on attempting to recreate the conditions in which the protein becomes unfolded and complexed with oleic ions. Such work has focused on using pure proteins including recombinant variant versions of the base proteins to facilitate the production of active complexes. Such starting materials however can also increase the cost of production.

The applicants have found that compositions having useful biological activity can be prepared directly from milk or from crude extracts of milk. Activity of such compositions is believed to be due to the presence of complexes such as HAMLET or BAMLET, but other active components may be present.

Thus a second aspect of the invention provides a composition comprising:
(a) milk or a crude protein-containing extract thereof;
(b) a fatty acid or lipid or a salt thereof; and
(c) an acidifying agent in an amount that is sufficient to reduce the pH of the composition to less than 4;
wherein the composition has been heat-treated.

Compositions of this type have been found to be biologically active and in particular appear to target and kill tumour cells in preference to healthy cells in a similar manner to HAMLET. The level of activity cannot be entirely explained by the presence of some HAMLET complex in the composition. Thus it appears that, surprisingly, other components of the milk or crude milk extract do not interfere with the HAMLET-like activity, and that other components contained in the composition may be enhancing the efficacy of the composition. By using milk or crude extracts in the preparation of active compositions rather than pure proteins, the cost of the starting materials is reduced.

In a particular embodiment in the composition of the second aspect of the invention, component (a) is a crude protein-containing extract of milk. The expression "crude protein-containing extract" refers to compositions obtained from milk using simple physical or chemical procedures or combinations of these, without the need for significant purification utilising processes such as purification or ion exchange columns. For instance, a crude protein-containing extract may be obtained by defatting the milk for example using a centrifugation process in which heavy fats sink to the base of a centrifugation tube and so can be separated from lighter components such as proteins which remain in the supernatant.

Alternatively or additionally, a crude protein-containing extract may be obtained by subjecting milk to a precipitation such as an ammonium sulphate precipitation for example using an ammonium sulphate solution having a concentration of from 30-70% for example about 50% of a saturated solution. This has the effect of removing the substantially insoluble milk proteins, whilst leaving more soluble proteins in solution in the supernatant. In this instance, the supernatant forms a suitable crude protein-containing extract for use in the composition of the invention.

In a particular embodiment of the second aspect of the invention, the crude protein-containing extract used in the composition is one which has been both defatted and then subject to an ammonium sulphate precipitation as described above. Suitable fatty acids or lipids used as component (b) above include those known to provide biologically active complexes and are as described above. The amount of component (b) present in the composition is suitably in a molar excess of the protein or proteins present in component (a) that is able to form a complex with said component. Identification of such proteins can be effected by knowledge or information regarding the protein content of the proteins in the milk component used and then by investigation as to whether individual proteins form complexes with component (b). Such information may be available in the literature or it may be determined using routine experimentation.

However, if such information is not available or cannot be obtained, then the amount of component (b) present in the composition may be added in a molar excess of the total protein content. For instance, the molar excess of component (b) as compared to the amount of protein present in component (a) is at least 70 times, and in a particular embodiment is about 100 times. This can be determined using calculations based upon the amount of protein present in the extract that can form complexes including those which are biologically active with component (b) and as illustrated hereinafter.

The milk used in the composition or as a starting material for the crude protein-containing extract may be any milk such as human, bovine, caprine or ovine milk. In many countries, a most convenient source of milk will be cows, goats or sheep but in others, a convenient source of milk may be buffalo, including water buffalo, camels, yaks or mares. Whilst human milk appears to provide highly active compositions that may be used in pharmaceutical applications, for other uses and in particular nutraceutical applications, bovine, ovine or caprine milk are more suitable for producing large scale products. In a particular embodiment, the milk is bovine milk and in particular cows' milk.

Human milk for instance contains generally about 1% w/v protein, for instance from 0.9 to 1.1% w/v protein whereas cows' milk contains a higher percentage of proteins (up to 4% w/v protein), but this is variable depending upon factors such as the breed of cow and the diet on which they are fed and proteins levels of between 3.1 and 3.9% w/v may be typical amongst European cows.

Thus, the amount of component (b) added to a composition may be higher where the milk composition is derived from cows' milk as compared to that used for human milk as discussed above. However, account can be taken of any pre-treatment to which the milk has been subjected. For instance, an ammonium sulphate precipitation process as described above will remove certain proteins such as casein. Thus this remaining material will lack this protein component which does not have to be included in the calculation to determine what is an excess of component (b). It may be possible to further reduce this amount if a detailed analysis of the proteins is carried out. If the individual protein components and their amounts are known or understood, then it may only be necessary to take account of those proteins which are able to form complexes with component (b) as discussed above.

Proteins remaining in human milk after such a treatment that may form complexes with component (b) include α-lactalbumin, lactoferrin, lysozyme, serum albumin and b-lactoglobulin. Milk from other sources, such as cows' milk, may contain different components and in different amounts.

The acidifying agent used in the composition is suitably an inorganic acid such as hydrochloric acid provided this is suitable for pharmaceutical or food use. Sufficient acidifying agent is included to ensure that the pH of the composition is less than 4, for example from 1-4 such as 2 or 3 and in particular about 2.

It is known that complexes obtained using α-lactalbumin from sources other than human milk, and in particular, BAMLET, obtained using bovine α-lactalbumin shows a qualitatively similar effects on cells and in particular on tumour cells as HAMLET (see for instance, Rammer et al. (2010) Mol. Cancer Ther. 9(1) 24-32). The applicants have found that this is also the case with a range of cell types including DLD-1 and HT29 cells, which are colon cancer cells (see Example 2 hereinafter). Therefore, prophylactic effects demonstrated hereinafter using HAMLET would be similarly observed if BAMLET or compositions based upon BAMLET are used instead of HAMLET. The ready availability of bovine milk and the known efficacy of BAMLET mean that bovine milk may be a particularly preferred source of component (a) for the prophylactic or nutraceutical use described herein.

According to a third aspect, the invention provides a method for preparing a composition according to the second aspect, said method comprising obtaining milk or a crude protein-containing extract thereof, adding a molar excess of fatty acid or salt thereof and in particular oleic acid or a salt thereof, acidifying to a pH of less than 4, and heat treating the resultant mixture. The heat treatment is suitably carried out at a temperature of from 35-70° C., for example at about 50° C. A mixture of the components is suitably incubated at this temperature for a period of sufficient to ensure that the composition acquires the required biological activity, for example as a result of the formation of complexes between components (a) and (b). This will depend upon various factors including the nature of the components and the volumes, but will generally be in the region of from 20 to 60 minutes, for example for 30 minutes.

Thereafter, the sample may optionally be subject to a purification technique such as dialysis, for example against phosphate-buffered saline and/or water overnight in order to remove impurities. This may be particularly useful if the composition is intended for pharmaceutical application. However, for nutraceutical applications, there may not be any need for a further purification, in particular if all components used in the preparation of the composition are suitable for food use.

The resultant composition may be used directly or it may be dried, lyophilised or freeze-dried for storage. The resultant powdered form of the composition may be particularly useful for use as a food additive in the preparation of nutraceutical products. It may for example be added in such a dried form to suitable food compositions such as dairy products, in particular products such as yoghurt, milk, powdered milk including formula milk such as infant formula milk, condensed milk, evaporated milk, crème fraiche, khoa, cheese, cottage cheese, ricotta, butter or ghee.

As discussed above, in a particular embodiment, component (a) of the composition is a crude protein-containing milk extract. The preparation of such a crude extract may form a preliminary step in the process of the invention. Thus, the method of the third aspect of the invention may further comprise the preliminary steps of (i) defatting milk for example by centrifugation, and/or (ii) removing milk proteins using a precipitation process such as an ammonium sulphate precipitation process as described above. Thereafter, the crude protein-containing extract for use in the composition is obtained by (iii) collecting the supernatant, for example by centrifugation.

Compositions of this type may be used in prevention of cancer of the gastrointestinal tract as discussed above. However, they may also have additional uses in the therapeutic or preventative treatment of a variety of conditions including those previously reported as being treated using complexes such as HAMLET. This includes bacterial infections, viral infections, papillomas and various forms of cancer including glioblastoma and mucosal cancers such as bladder cancer and colon cancer. In a particular embodiment, the compositions are used for the treatment of cancer. For such applications, the compositions can be applied topically where appropriate, or orally.

Alternatively, as described above, the compositions of the invention may be used as a nutraceutical for oral administration as part of a normal diet. These will provide nutritional benefits and may further protect against diseases such as gastrointestinal cancers, as well as bacterial and viral infections.

Thus a fourth aspect of the invention provides a method for preventing or treating proliferative disease such as cancer, said method comprising administering to an individual in need thereof an effective amount of a composition of the second aspect of the invention.

The composition is suitably administered orally where appropriate, for example for the treatment or prevention of gastrointestinal cancer such as colon cancer. However, in other applications, for example for the treatment of skin papillomas or cancers such as bladder cancer that are not found in the gastrointestinal tract, the composition is suitably administered topically.

The amount of composition administered to an individual will depend upon a variety of factors including the nature of the composition as well as the risk factor. However, as a general rule from 1 µg to 100 milligram/dose of the biologically active complex is used for each administration, which is suitably administered daily.

Importantly however, the complex of the first aspect as well as the composition of the second aspect of the invention is used in the prevention of cancers of the gastrointestinal tract. Thus in a fifth aspect the invention, there is provided a method for preventing the formation of cancer of the gastrointestinal tract, which method comprises administering to an individual a biologically active complex as described above or a composition containing such a complex such as a pharmaceutical or nutraceutical composition as well as a composition derived from milk as described above. The amount of complex administered to an individual will depend upon a variety of factors including the nature of the composition as well as the risk factor. However, as a general rule from 1 µg to 200 mg/dose for example from 2 to 200 mg/dose or from 1 µg to 100 milligram/dose of the biologically active complex is used for each administration, which is suitably administered daily.

A significant number of individuals inherit the susceptibility to colon cancer but despite repeated, often invasive diagnostic and therapeutic procedures, many develop colon cancer. Localized primary tumors are mostly subjected to surgical removal and drug development targets metastatic disease. Even though susceptible individuals may be identified by screening for APC mutations, prophylactic drugs that prevent familial disease are not available. The prophylatic and therapeutic effects of HAMLET demonstrated in the examples below are therefore of great potential significance. APC$^{Min/+}$ mice carrying the human mutation were used as a model and their spontaneous, age related tumor development was drastically reduced by peroral HAMLET prophylaxis. Furthermore, in mice with established tumors, HAMLET reduced tumor numbers, size and mortality. These effects were accompanied by reduced levels of β-catenin and β-catenin-dependent proteins and gene expression analysis suggested that surviving tumor cells had been routed to a more benign phenotype with reduced Wnt signaling and increased aerobic glycolysis. The effects on β-catenin were explained by ion channel- and caspase dependent mechanisms. HAMLET thus offers a new approach to colon cancer therapy, purging established and emerging tumor cells from the intestinal mucosa. Peroral HAMLET administration would be expected to have clinical benefits, especially in FAP families bearing the mutated APC gene.

Aberrant activation of Wnt/β-catenin signaling is fundamental to the pathogenesis of colon cancer and molecular control of this pathway has become a major therapeutic focus. In normal cells, proteasomal β-catenin degradation proceeds through the formation of a destruction complex, limiting the transcription of β-catenin-dependent genes. In colon cancer cells, β-catenin degradation is impaired and nuclear translocation is enhanced, leaving the Wnt-signaling pathway overactive and the cells tumor prone. Extracellular Wnt inhibitors, including the secreted Frizzled-related proteins (SFRPs) have been pursued as potential therapeutics and small molecular antagonists of the protein-protein interaction between β-catenin and Tcf transcription factors have shown encouraging pre-clinical results. In addition, numerous epidemiological studies have detected benefits of non-steroidal anti-inflammatory drugs (NSAIDs) with a molecular mechanism recently linked to inhibition of nuclear accumulation of β-catenin. In response to HAMLET, β-catenin was proteolytically cleaved and the nuclear β-catenin content was markedly reduced. Remaining polypose tissue from HAMLET treated mice showed a reduction in β-catenin-, VEGF-, Cox-2-staining as well as proliferation markers. These findings identify HAMLET as a new Wnt pathway modifier, which also adds the activation of death pathways unrelated to Wnt.

HAMLET activates ion fluxes and ion channel inhibitors blocking such fluxes rescue tumor cells from HAMLET induced death (Storm et al., Plos one (2013), 8, 3, e58578). This ion channel dependence was confirmed here as ion flux inhibitors rescued colon cancer cells from death. In addition, caspase-3 activation and β-catenin fragmentation required ion channel activation, suggesting that ion channels are activated upstream of the other end points. A similar pattern of β-catenin fragmentation in colon cancer was previous described but most studies have focused on proteasomal destruction of β-catenin, resulting from GSK3 phosphorylation. HAMLET treatment did not alter the levels of phosphorylated or total GSK3, however. HAMLET has previously been shown to trigger caspase activation and an apoptotic response in tumor cells, with blebbing, mitochondrial depolarization and cytochrome C release and annexin exposure. The functional importance of this response has been unclear, however, as caspase inhibition does not prevent cell death. Furthermore, p53 mutations and Bcl2 or Bcl$_{XL}$ genotype variation does not alter the HAMLET sensitivity of carcinoma cells, further emphasizing apoptosis as a response not involved in cell death. This study suggested a function for caspase-3 as a mechanism of β-catenin fragmentation rather than cell death.

The lack of selectivity for tumor tissue is a major concern in current colon cancer therapy and side effects can be dramatic. In the present study, HAMLET was taken up by tumor tissue but not by adjacent, healthy tissue, suggesting that HAMLET reaches the intestinal polyps in APC$^{min}$ mice after peroral administration, thereby interacting with tumor tissues and killing tumor cells. In addition, HAMLET was detected in intestinal contents up to six hours after administration, reflecting the relative resistance of the fatty acid bound form of α-lactalbumin to intestinal proteases. Furthermore, we found no evidence of toxicity for intestinal tissue, consistent with HAMLET being a human milk constituent. Previously, tumor-bearing animals with glioblastoma or bladder cancer showed no toxic responses to HAMLET and no adverse effects on animal behavior were registered. Human studies of skin papillomas and bladder cancer also suggested that the low toxicity is maintained in vivo.

Peroral HAMLET administration presents a conceptually new therapeutic approach in colon cancer, potentially killing tumor cells and shifting surviving cells to a more benign phenotype. Based on this activity spectrum, the use of HAMLET and its variant forms as an oral prophylactic would be of great value, especially in families genetically prone to colon cancer.

DESCRIPTION OF THE DRAWINGS

The invention will now be particularly described by way of example with reference to the accompanying figures which are summarized as follows:

(FIG. 1A) Dissection photomicrographs of small intestinal segments showing a decrease in tumor numbers (arrowhead) in HAMLET treated mice. (FIG. 1B) Quantification of HAMLET's effect on tumor number and size (, P<0.01) (FIG. 1C) Methylene blue stained whole mounts of intestinal segments shows reduced tumor (arrowhead) numbers in HAMLET-treated mice. (FIG. 1D) H & E stained intestinal Swiss rolls showing smaller and fewer polyps in HAMLET-treated APC$^{min}$ mice. (FIG. 1E) Kaplan-Meier survival analysis. The endpoint was reached when mice were moribund or at 40 weeks. (FIG. 1F) HAMLET-treated mice (n=15) showed improved survival compared to mock treated mice (n=15) (, P<0.01) FIG. 2A-H. HAMLET treatment reduces WNT/β-catenin pathway proteins levels, suppresses proliferation and is resistant to digestion by gastric enzymes.

FIG. 3A-E. Whole genome profiling identifies distinct transcriptional events in HAMLET-treated tumors Five weeks after HAMLET-treatment, existing tumors in treated and mock groups were excised and totalRNA was extracted and hybridized to Affymetrix MG430 whole genome arrays. (FIG. 3A) Heatmap showing the top 500 differentially expressed genes between HAMLET and mock treated, indicating that there are distinct differences between the two groups. (FIG. 3B) Pathway analysis of differentially expressed genes using GSEA or Ingenuity Pathway Analysis highlighted WNT signaling and Glycolytic pathway as enriched in HAMLET-treated tumors. (FIG. 3C-D) GSEA results showed that the Glycolytic pathway and WNT Signalling pathway are enriched in HAMLET treated tumors. (FIG. 3E) Schematic representation of metabolites and enzymes that were upregulated in HAMLET-treated tumors.

(FIG. 4A) Morphological changes in response to 35 µM HAMLET was examined by phase contrast holographic microscopy. HAMLET caused rapid rounding and detachment of colon cancer cells in a time dependent manner (FIG. 4B) Dose dependent loss of viability in human colon cancer cells (DLD1) after HAMLET treatment (3 hours), quantified by ATP measurements and Prestoblue. * p<0.05, * p<0.001. (FIG. 4C) Decrease in β-catenin, cyclin D1 and VEGF protein levels in DLD1 cells after HAMLET treatment (3 hours, 0.5 mg/ml). β-actin was the loading control. (FIG. 4D) HAMLET treated cells had lost nuclear β-catenin (green) staining. The uniform cytoplasmic staining was replaced by strong staining at the cytoplasmic membrane. DLD1 cell monolayers were treated with HAMLET (1 and 3 hours), fixed, immunostained for β-catenin (green) with nuclear DRAQ5 counterstaining (red). HAMLET significantly reduced nuclear β-catenin staining in treated cells.  p<0.01 ** p<0.01. (FIG. 4E) Dose dependent degradation of β-catenin HAMLET (FIG. 4F) IP for 1 hour 35 µM HAMLET treated cells (FIG. 4G) Dephosphorylation of β-catenin in response to 3504 HAMLET treatment in a time dependent manner. (FIG. 4H) Time dependent cleavage of caspase 3 in DLD-1 cells but with no effect on GSK3 phosphorylation.

(FIG. 5A) DLD-1 cells were pretreated with inhibitors of ion channels (Amiloride and $BaCl_2$) or caspases (zVAD and leupeptin) as indicated and subsequently HAMLET-treated (35 µM, 1 hour). Ion channel inhibitors as well as zVAD abrogated b-catenin cleavage but not leupeptin. (FIG. 5B) HAMLET-induced (35 µM, 1 hour) loss of nuclear β-catenin staining (green) was prevented by pretreatment with ion channel inhibitors. Nuclei are stained red with Draq5. (FIG. 5C) A TOP-flash dual luciferase reporter assay was used to quantify β-catenin-dependent promoter activity in HAMLET treated versus control cells. A dose dependent reduction in luciferase activity was detected after 3 hours of HAMLET treatment.

(FIG. 6A) Dissection photomicrographs of small intestinal segments showing prevention of tumor development (arrowheads) in HAMLET treated mice. (FIG. 6B-C) H & E stained intestinal Swiss rolls showing smaller and fewer polyps in $APC^{min}$ mice receiving HAMLET prophylaxis. (FIG. 6D) Quantification of tumor number and size (, P<0.01). (FIG. 6E) The HAMLET group mice (n=10) showed prevention of tumor development compared to mock treated mice (n=10) (, P<0.01)

EXAMPLE 1

Figure 1A:
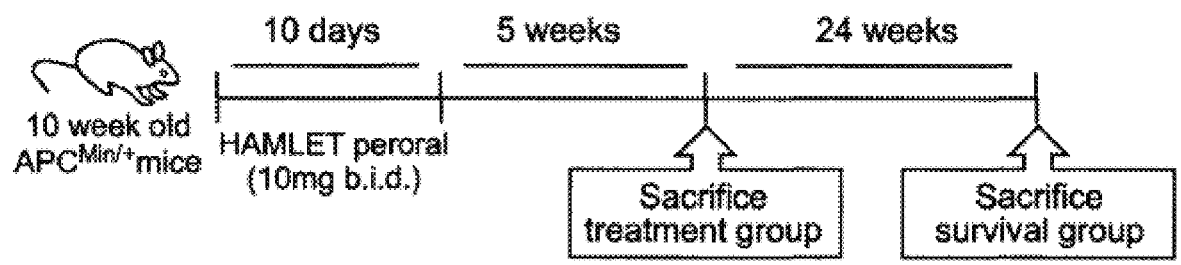
FIG. 1A-F. HAMLET treatment reduces intestinal tumor development and increases survival. APC$^{min}$ mice were treated with 10 mg of HAMLET, twice daily for 10 days and sacrificed 5 weeks after the end of treatment or observed for survival analysis until 40 weeks of age.

Prevention of Colon Cancer
Material and Methods
HAMLET Production

HAMLET was produced as described (Svensson M. et al. Proc Natl Acad Sci USA 97: 4221-4226. Briefly, native α-lactalbumin was purified from human milk by hydrophobic interaction chromatography. The protein was unfolded with EDTA, subjected to ion-exchange chromatography on a matrix pre-conditioned with oleic acid and eluted with high salt. HAMLET was lyophilized after purification and kept frozen until use.

Cell Culture and Cell Death Assays

Colon carcinoma cells (ATCC, Manassas, VA) were cultured in RPMI-1640 with non-essential amino acids (1:100), 1 mM sodium pyruvate, 50 µg/ml, gentamicin (all from Gibco, Paisley, UK), and 5% (A549 and A498) or 10% (HeLa and Jurkat) fetal calf serum (FCS), respectively.

In Vivo Treatment with HAMLET $Apc^{Min/+}$ mice were obtained from Jackson Laboratories and bred in Biological Resource Center, Biopolis, Singapore or the animal facility, MIG, Lund University, Sweden. For the detailed treatment protocol, see FIG. 7. Eight to ten week-old male mice were orally gavaged with 10 mg of HAMLET in 400 µl PBS, twice daily for ten days. Mice were not given water or feed 5 hours prior to HAMLET administration. Feed and water were provided 30 minutes after HAMLET oral administration. Mice were sacrificed 5 weeks after the end of HAMLET treatment and intestinal tissue samples were collected for further analysis. A similar treatment was used in the survival study groups where mice were observed until 40 weeks of age. All procedures were in accordance with Institutional Animal Care and Use Committee's recommendations.

Tumor Enumeration and Sample Collection

Mice were sacrificed by $CO_2$ inhalation; blood and spleens were collected for analysis. The entire gastrointestinal tract was removed and kept in ice cold PBS for dissection. The stomach and caecum were not included in the analysis due to low tumor incidence. The small intestine was cut into 3 equal length segments. To remove intestinal contents, each segment was flushed with ice cold PBS with the help of a gavage needle attached to a syringe. Each segment was kept on a filter paper and longitudinally opened. Tumor numbers and size were determined using an Olympus dissecting microscope.

Methylene Blue Staining

The opened intestinal segments were spread flat between sheets of filter paper and fixed overnight in 10% neutral buffered formalin. Formalin-fixed sections were transferred to 70% ethanol and stained with 0.2% methylene blue. Stained sections were rinsed in deionized water and imaged by dissecting microscopy.

Immunohistochemistry

Swiss rolls of longitudinally opened intestinal segments were fixed overnight in 10% neutral buffered formalin. Samples were embedded in paraffin and 5 µm thick sections were further processed for immunohistochemistry. For immunocytochemistry cells were grown on 8 chamber glass slide (Lab-Tek, Chamber Slide, Thermo Fisher Scientific) at a concentration of $5\times10^4$ cells per well for overnight at 37° C. All cells were permeabilized (0.1% Triton X-100 dissolved in 5% FCS-PBS, 10 min), blocked (10% FCS, 1 h) and stained with anti β-catenin antimouse antibody (1:50 dilution, BD Bioscience) overnight at 4° C. followed by secondary antibody labeled with Alexa-Fluor 448 (1:200, Molecular Probes) for 1 h. DRAQ-5 (Bioscience, San Diego, CA) was used as nuclear stain (1:500, 5 min). Cells were mounted with mounting media (Fluoromount, Sigma) and Fluorescence was detected in a LSM 510 DUO confocal microscope (Carl Zeiss). For Phase holographic Imaging, HoloMonitor™ M2 digital holographic microscope (Phase Holographic Imaging AB, Lund, Sweden) was used which records 3D structure of cells by their exposure to 0.8 mW HeNe laser (633 nm) using interfering wave fronts induction.

In Vivo HAMLET Uptake

After 5 hrs of starvation, mice were orally gavaged with 10 mg HAMLET in 400 µl PBS. After 2, 4 and 6 hours of HAMLET administration, mice were sacrificed with $CO_2$ inhalation. To detect HAMLET in the intestinal lumen, 5 cm intestinal segments from upper or lower small intestine were harvested and washed with 500 µl of ice cold PBS. SDS lysis buffer (2%) was added and the intestinal washing were heated (5 min, 95° C.), vortexed, heated again and centrifuged at high for 10 minutes. Supernatant was collected and used for Western blots for the detection of HAMLET.

For the detection of HAMLET in tumor tissue, intestinal segments were flushed thoroughly (5 ml PBS, 3×) to remove luminal contents. Segments were longitudinally open and again washed in PBS (5 ml PBS, 3×).

Western Blots

Tumors and healthy intestinal tissue was collected and kept at −80° C. Tissue lysates in 2% SDS buffer were subjected to SDS-PAGE and electroblotted to a PVDF membrane. Membranes were than incubated with primary antibodies including β-catenin (1:4000, BD Biosciences), p-β-catenin (1:1000, Cell Signaling), actin (1:2000, Sigma), GAPDH (1:4000, Novus Biologics) and visualized using ECL (Amersham Biosciences, Piscataway, NJ).

Measurement of COX-2 and VEGF Activity

COX-2 activity was measured according to the manufacturer's instructions (Cayman Chemicals). Briefly, intestinal samples were homogenized in ice-cold lysis buffer (0.1M Tris-HCl, pH 7.5, supplemented with protease inhibitor mixture (Sigma-Aldrich)) for 20 seconds. The homogenates were centrifuged (10,000×g, 15 min, 4° C.), the supernatants collected and stored at −80° C. for subsequent analysis. The results were corrected for the DNA content of the tissue sample and expressed as fold increase over control. VEGF was quantified by ELISA in intestinal tumor tissue after rinsing with PBS, homogenization and overnight storage at −20° C. Two freeze-thaw cycles were performed to break cell membranes and homogenates were centrifuged (5,000× g, 5 min, 4° C.) and stored at −80° C. for subsequent analysis. ELISA was performed according to manufacturer's instructions (Quantikine Mouse VEGF, R&D Systems), cut off >3.0 µg/mL.

Liver Function Test

Serum ALT and AST activity was determined by Infinity ALT Reagent and Infinity AST Reagent (both from Thermo Scientific) according to the manufacturer's instructions.

Confocal Microscopy

Cells were cultured overnight in RPMI-1640 with non-essential amino acids (1:100), 1 mM sodium pyruvate, 50 µs/ml Gentamicin (all from PAA, Pasching, Austria) and 10% fetal calf serum (FCS) on 8-well chamber slides (Nalge Nunc, Rochester, NY). The cells were incubated with HAMLET (0.3 or 0.5 mg/ml, 1 and 3 hours) in serum-free RPMI-1640 (FCS was added after 1 hour) and fixed with 3.7% formaldehyde. Detached cells were centrifuged onto microscope slides (Menzel-Gläser Polysine slides, Thermo Scientific, Braunschwieg, Germany) using a Cytospin (500 rpm, 5 min), permeabilized with 0.25% Triton X-100/5% FCS/PBS for 10 min and stained with anti-β-catenin (1:20, Santa Cruz Biotechnology, Santa Cruz, CA, USA), anti-cyclin D1 (1:50, Santa Cruz Biotechnology, Santa Cruz, CA, USA), anti-Ki-67 (1:50, BD Bioscience, Franklin Lakes, NJ, USA) or anti-Cox-2 (1:50, BD Bioscience, Franklin Lakes, NJ, USA) antibodies followed by Alexa-Fluor 488-labaled secondary antibody (anti-mouse, 1:100, Molecular probes, Eugene, OR, USA). For nuclear staining DRAQ5 (1:500, eBioscience, San Diego, CA) was used. Images were captured on a confocal microscope (LSM510 META, Carl Zeiss, Jena, Germany) with pinhole settings equal to 1 airy unit for fluorescence detection.

Transcriptomic Analysis

For the in vivo transciptomics analysis, tumors were collected 5 weeks after the end of treatment and stored in RNAlater (Ambion). Approximately 5 mgs of tissue were homogenized using a Tissuelyser (Qiagen) and totalRNA was extracted using RNeasy (Qiagen). For transcriptomic analysis, 300 ng of totalRNA was converted into cRNA using Affymetrix 3' IVT Express Kit as per manufacturers instructions. 10 µg of labeled cRNA were hybridized to Affymetrix MG-430 PM Array Strips. After hybridization and washing, the fluorescence intensity was measured in the Affymetrix Gene Atlas system. Array data were normalized using the robust multichip average (RMA) and filtered for expression values lower than $2^5$. Differentially expressed genes were identified, by fitting the normalized data to a linear model and the 500 genes showing lowest p-values were considered differentially expressed. To identify functionally relevant alterations, the gene list was submitted to Ingenuity Pathway Analysis. Gene set-enrichment analysis (GSEA) was performed by the use of the Canonical Pathways Geneset collection v. 2.5 (broadinstitute.org/gsea/msigdb/indexjsp). The microarray dataset reported here has been deposited in NCBI's Gene Expression Omnibus and will be accessible at time of publication.

Statistical Analysis

Data are expressed as means±SEMs. Treated and control groups were compared with use of the two-sided Student's t-test and the chi-square test with Yates' correction and 1 degree of freedom. Differences in survival were evaluated by Kaplan-Meier analysis with a Gehan-Breslow-Wilcoxon test.

Results

HAMLET Reduces Tumor Burden and Increases Survival

Figure 1B:
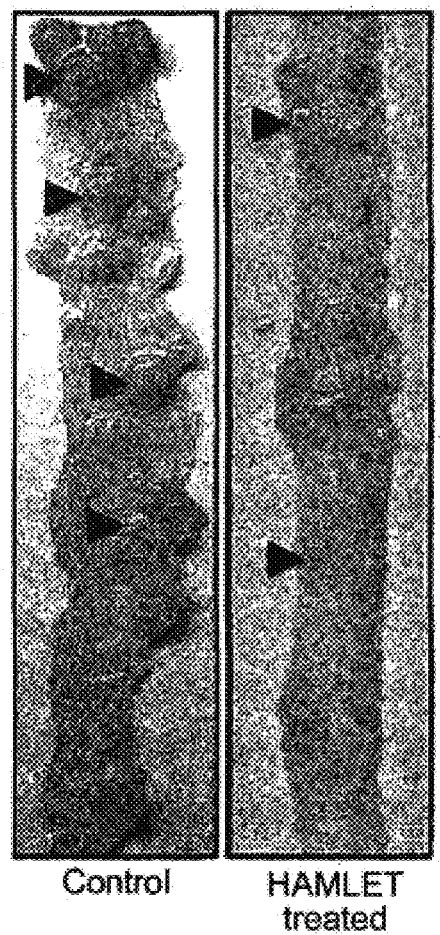
Figure 1C:
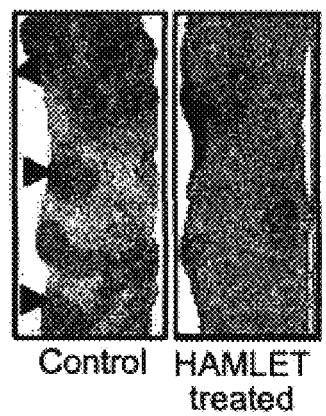
Figure 1D:
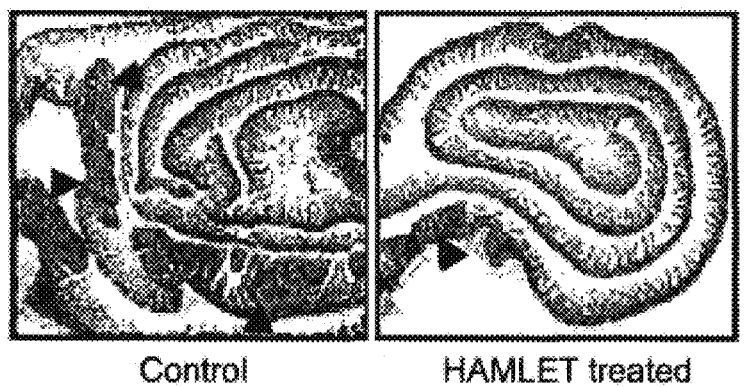
Figure 1E:
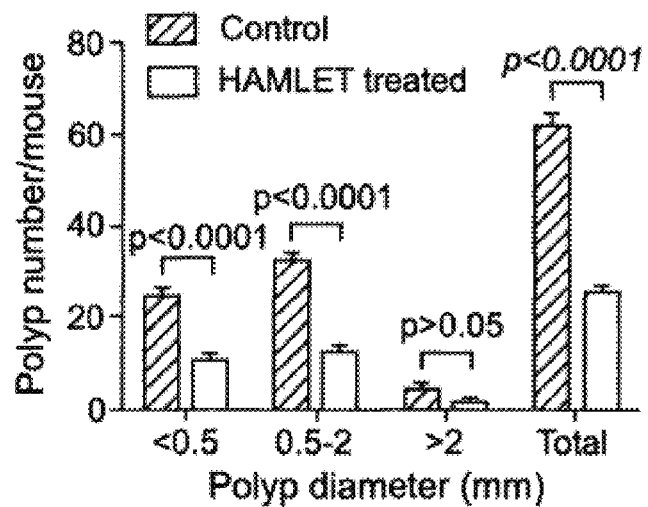
Figure 1F:
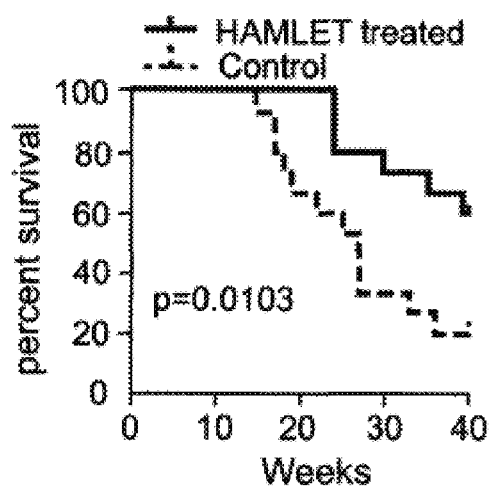
Figure 7:
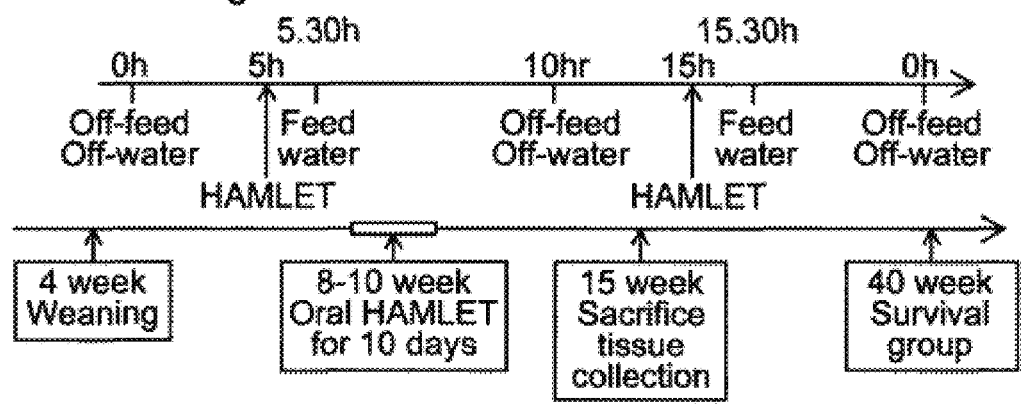
FIG. 7. Treatment regimen for the use of HAMLET as a peroral therapeutic. Eight to ten week-old male mice were orally gavaged with 10 mg of HAMLET in 400 µl PBS, twice daily for ten days. Mice were sacrificed 5 weeks after the end of HAMLET treatment and intestinal tissue samples were collected for further analysis.
Figure 8:
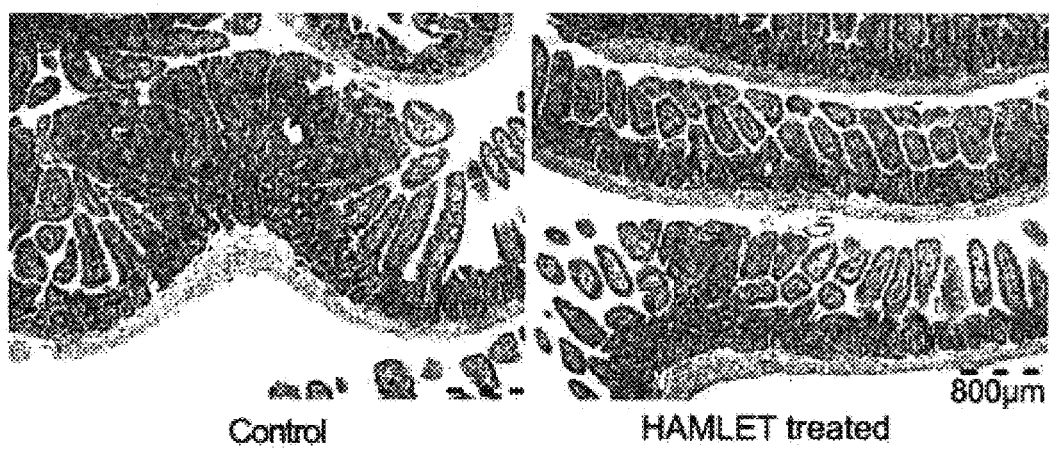
FIG. 8. Histology of H&E stained intestinal sections from HAMLET treated and control APC min mice. Intestinal villus hyperplasia was noticed in untreated—but not in HAMLET-treated mice.

HAMLET was administered perorally to tumor-bearing $APC^{Min/+}$ mice (10-12 weeks of age) and tumor development was assessed, five weeks after the end of treatment (FIG. 7). Peroral HAMLET administration caused a significant reduction in the number of tumors and in tumor size compared to untreated mice (FIG. 1A-E). Quantification by low magnification light microscopy of intestinal segments opened longitudinally showed that the total number of polyps was reduced by about 60% in the HAMLET treated group (FIG. 1B, p<0.01). A reduction in polyp number and size was also evident in methylene blue stained sections of intestinal segments (FIG. 1C). H&E staining of "swiss roll" sections of the intestinal segments showed significant differences compared to untreated mice, as fewer and smaller tumors were observed (FIG. 1D). Intestinal villus hyperplasia was noticed in untreated mice but treated mice showed normal villi (FIG. 8). Furthermore, the peroral HAMLET regimen also protected the mice against tumor-associated mortality, shown as a Kaplan-Meyer curve until 40-weeks of follow up FIG. 1E (p<0.01).

Reduced Levels of β-Catenin Pathway Proteins in Treated Tumors

To examine if the effects of HAMLET could be explained by modulation of the Wnt signaling pathway, β-catenin and β-catenin-dependent proteins were quantified in tumor biopsies five weeks after initiation of HAMLET treatment. Tissue sections obtained from HAMLET treated or control tumors were stained with specific antibodies and peroxidase-labeled secondary antibodies (FIG. 2A). β-Catenin staining was markedly reduced in the HAMLET treated tumor tissue, compared to untreated controls. This difference in β-catenin levels was confirmed by Western blots on tumor tissue homogenates (FIG. 2B), suggesting that HAMLET causes a reduction in β-catenin protein levels.

Figure 2A:
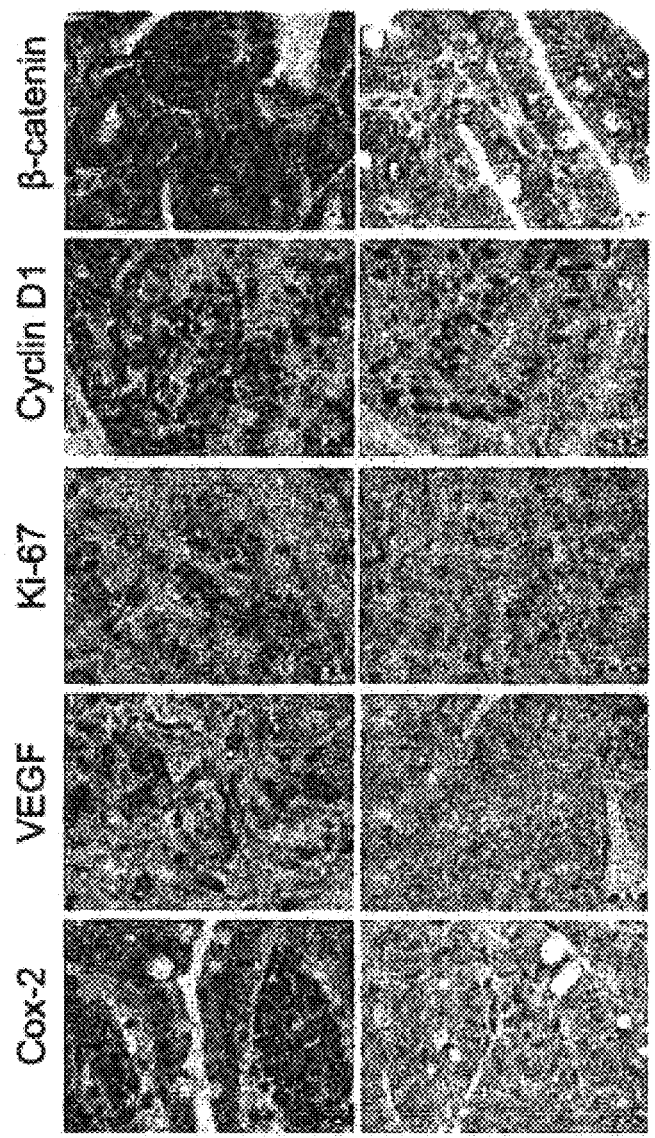
(FIG. 2A) Immunohistochemistry demonstrating reduced staining for β-catenin, Cyclin D1, VEGF, Cox-2 and Ki-67 in HAMLET treated-compared to mock-treated tumors.
Figure 2B:
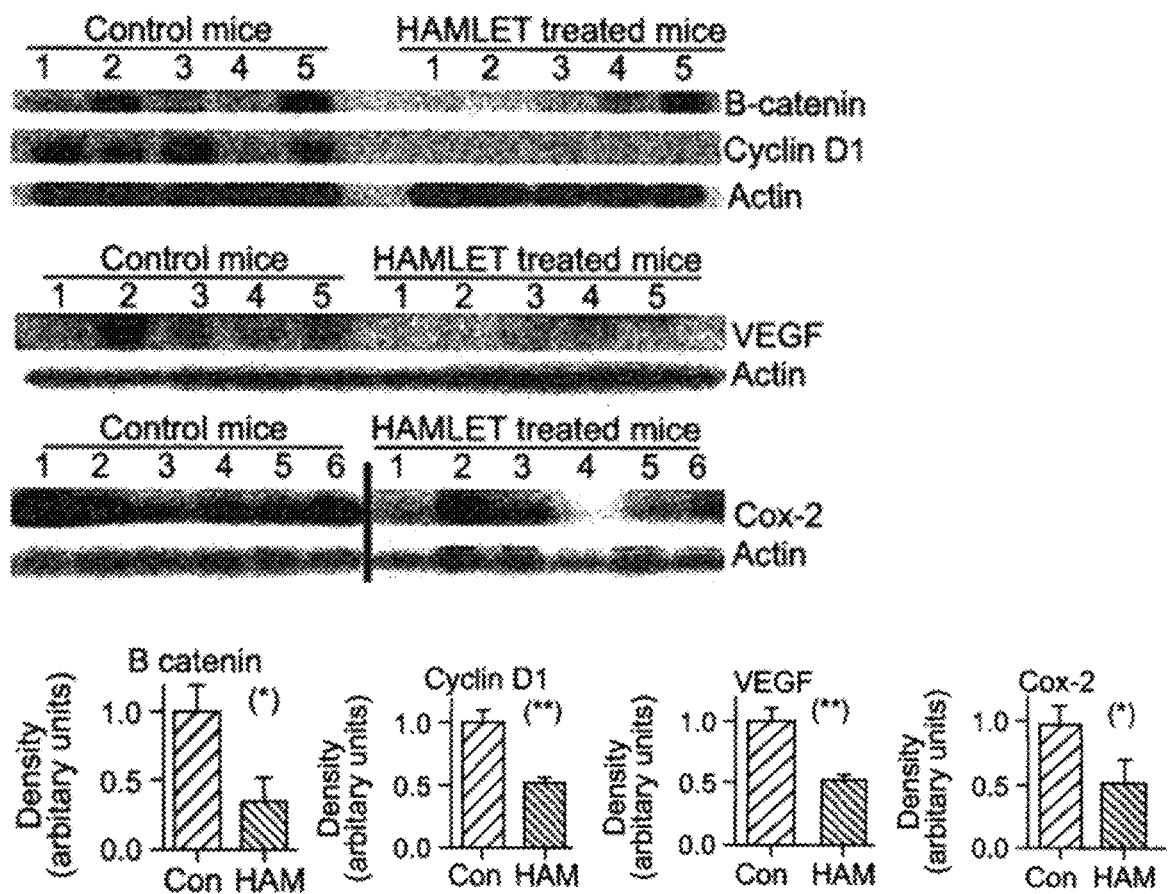
(FIG. 2B) Western blots showing reduced levels of β-catenin, Cylin D1, VEGF and Cox-2 in HAMLET treated—compared to mock-treated tumors. Histograms show the mean densitometry values for the blots of each protein (*, P<0.05; **, P<0.01). Quantification of (FIG. 2C) Ki-67, (FIG. 2D) VEGF and (FIG. 2E) Cox-2 in tumor lysates.
Figure 2C:
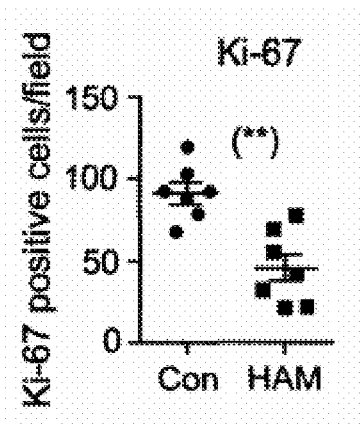
(FIG. 2F) Immunostaining, using anti-α-lactalbumin antibodies shows intense staining in intestinal polyps (arrowhead) representing high HAMLET uptake by tumor tissue (4 hours). Neighboring healthy tissue (arrow) shows weak staining suggesting low HAMLET uptake.
(FIG. 2G) Western blot detecting tissue uptake of HAMLET (4 hours). Small intestines were washed with PBS, tumors and normal tissues were collected separately for western blotting. The tumors contained higher amounts of HAMLET than adjacent healthy tissues. β-actin was the loading control. USI, upper small intestine; DSI, distal small intestine.
(FIG. 2H) Stability of HAMLET in the intestine. After oral HAMLET gavage (2, 4 and 6 hours), luminal contents were collected from the stomach and small intestinal segments for western blotting using anti-α-lactalbumin antibody. β-actin was the loading control.
Figure 2D:
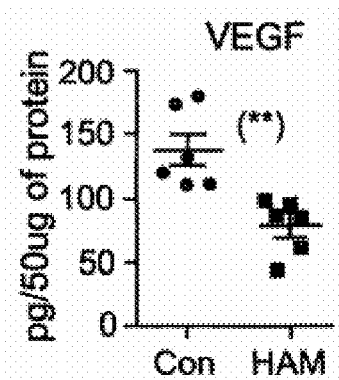
Figure 2E:
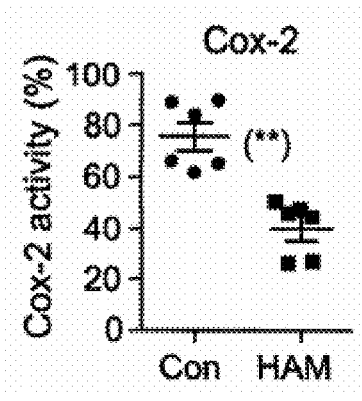

To examine if HAMLET modifies the expression of proteins downstream of β-catenin, tissue sections obtained from HAMLET treated or control tumors were stained with Cyclin D1, Cox-2 and VEGF-specific antibodies (FIG. 2A). Cyclin D1 staining was reduced in tumors from HAMLET treated—compared to untreated mice and VEGF and Cox-2 staining showed a similar pattern (FIG. 2B). This reduction in Cyclin D1 protein levels was confirmed by western blots (p<0.01) and the reduction in VEGF and Cox-2 activity by ELISA of tissue extracts (FIGS. 2D and 2E, p<0.01). Finally, a marked reduction in the frequency of Ki-67 positive cells (FIG. 2C) suggested that proliferation is reduced in HAMLET treated—compared to untreated tumors.

The results suggest that HAMLET treatment reduces β-catenin levels as well as the expression of β-catenin dependent proteins in surviving tumor cells.

HAMLET is Taken Up by Tumor Cells and is Resistant to Gastric Enzymes

Figure 2F:
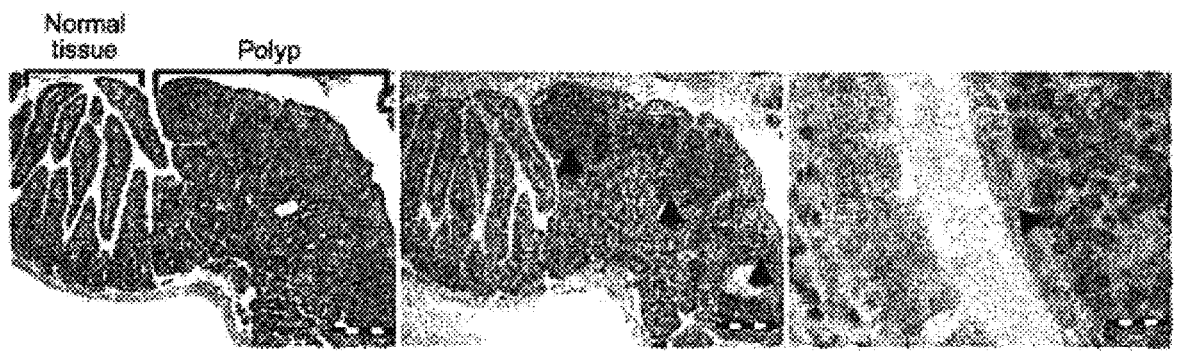
Figure 2G:
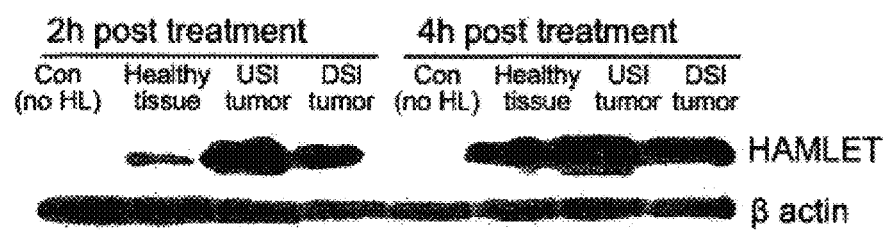

The uptake of HAMLET from the gastrointestinal lumen into tumors was visualized in formalin fixed tissue sections, 6 hours after HAMLET administration. HAMLET was shown to accumulate in the tumors (FIG. 2F), with strong nuclear staining. Most adjacent healthy cells were negative but some crypt cells showed weak nuclear HAMLET staining, suggesting a low degree of uptake by these rapidly proliferating cells. Differences in HAMLET uptake between polyps or healthy tissue from individual mice were confirmed by western blots of tissue extracts (FIG. 2G).

Figure 2H:
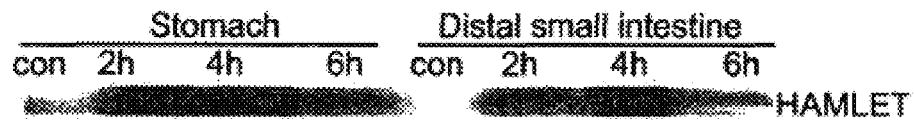

To examine if HAMLET resists proteolytic degradation in vivo, gastro-intestinal contents were harvested after HAMLET gavage and subjected to western blots, using alpha-lactalbumin-specific antibodies (FIG. 2H). Bands of 14 kDa were detected in the contents of the stomach and distal small intestine, 6 hours after oral administration, suggesting that part of the HAMLET complex remains intact in the gastro-intestinal tract.

Whole Genome Profiling Identifies Distinct Transcriptional Events in HAMLET-Treated Tumors The long-term, in vivo response to HAMLET was further characterized by whole genome transcriptional profiling of tumors excised from HAMLET treated mice or mock treated controls. Total tumor RNA from eight animals (5 weeks after treatment) was hybridized to Affymetrix MG-430 PM Arrays and functionally relevant transcriptional changes were identified using a comprehensive bioinformatics approach. To account for experimental variation, statistical testing (empirical Bayes moderated linear models) was applied between mock-treated and HAMLET-treated groups and the resulting gene lists were subjected to Ingenuity Pathway Analysis. Additionally, important pathways associated with the HAMLET-treated tumors were identified using Gene Set Enrichment Analysis (GSEA (Subramanian A, et al Proc Natl Acad Sci USA 102: 15545-15550). The 500 genes showing the lowest adjusted p-values are shown in FIG. 3A.

Figure 3C:
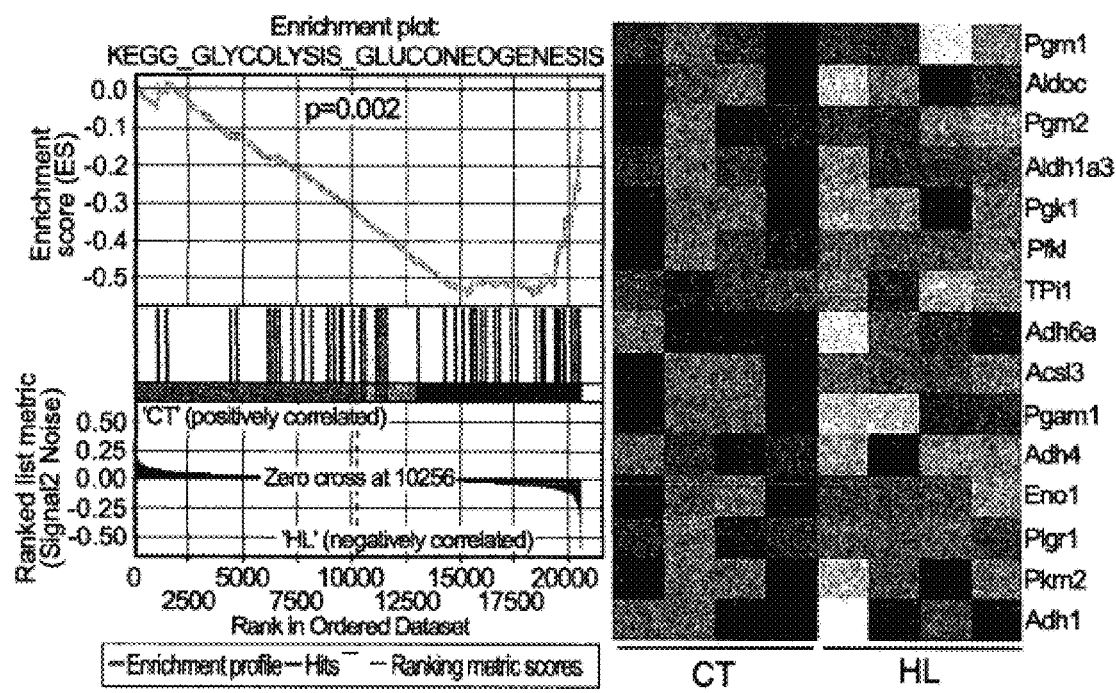
Figure 3D:
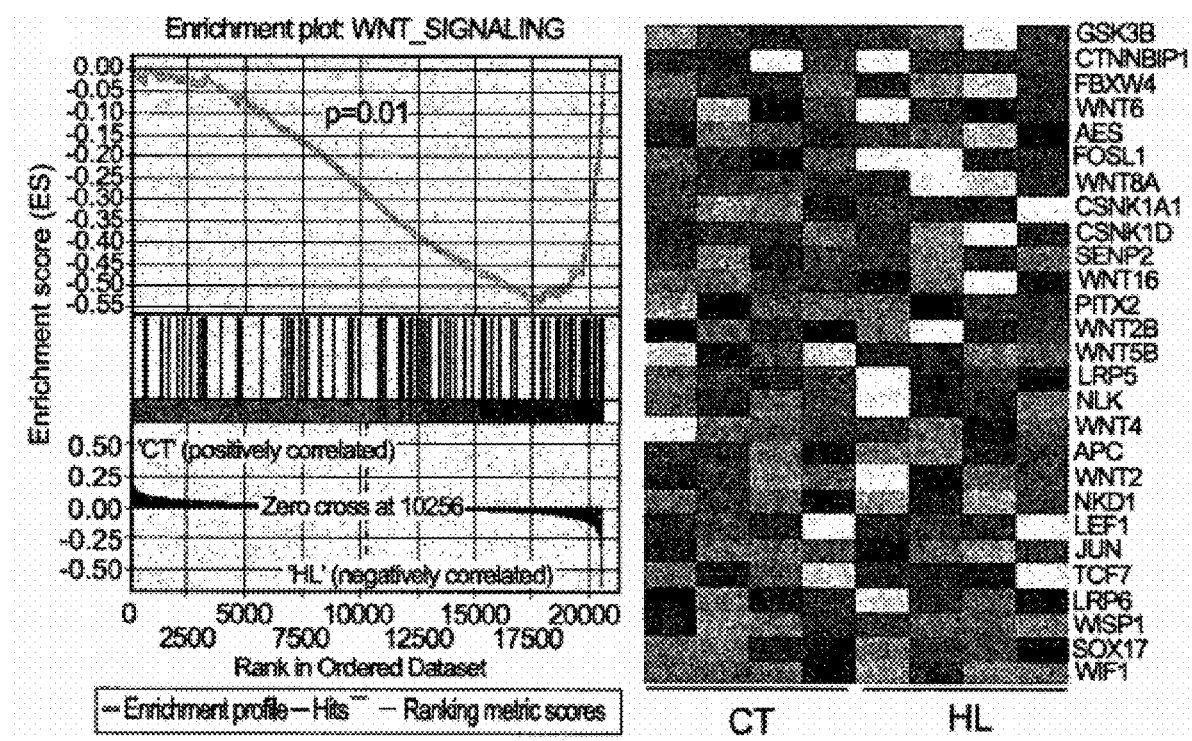
Figure 3E:
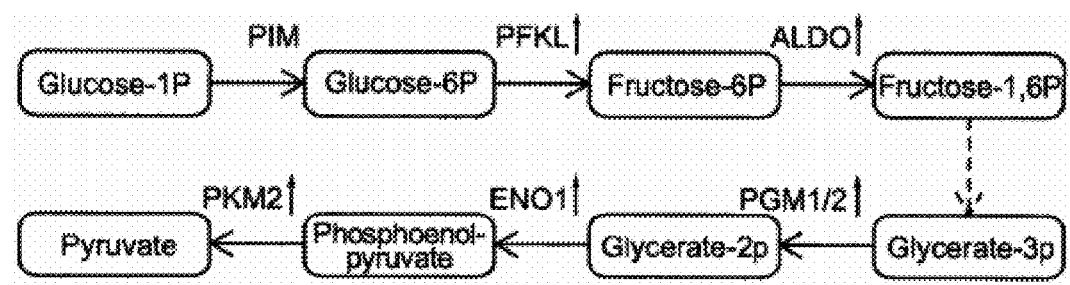

The most highly expressed genes in HAMLET treated tumors were involved in glucose metabolism (Ingenuity p-value=$10^{-9}$ and GSEA FDR q-value=0.05) and upregulated genes included a large fraction of key enzymes responsible for glycolytic fluxes. Phosphoglucomutase 1, phosphofructokinase, enolase, pyruvate kinase M2 and alcohol dehydrogenase were all upregulated (FIGS. 3C and 3E). GSEA analysis confirmed the high expression of glycolytic enzymes, but in addition, genes associated with the WNT signaling pathway were enriched in the HAMLET-treated tumors (q-values 0.032). In accordance with the inhibition of β-catenin in HAMLET treated tumors (FIG. 2B) the highly expressed genes were predominately negative regulators of this pathway. WNT inhibitory factor 1, a secreted protein containing a WNT inhibitory factor (WIF) domain and 5 epidermal growth factor (EGF)-like domains was upregulated twofold in HAMLET treated tumors as was SOXY17 (SRY (sex determining region Y-box 17), which modulates WNT signaling through binding to WNT3A. Other genes upregulated in the WNT signaling pathway included JUN, indicating a possible role for stress activated MAP kinases in HAMLET response. Interestingly, GSEA analysis also indicated increased expression of genes involved in retinol metabolism in tumors of HAMLET treated mice. Retinol has previously been shown to decrease β-catenin protein levels and β-catenin targets gene mRNA including c-Myc and Cyclin D1, implying that retinol processing may influence HAMLET's effects on β-catenin.

Figure 9:
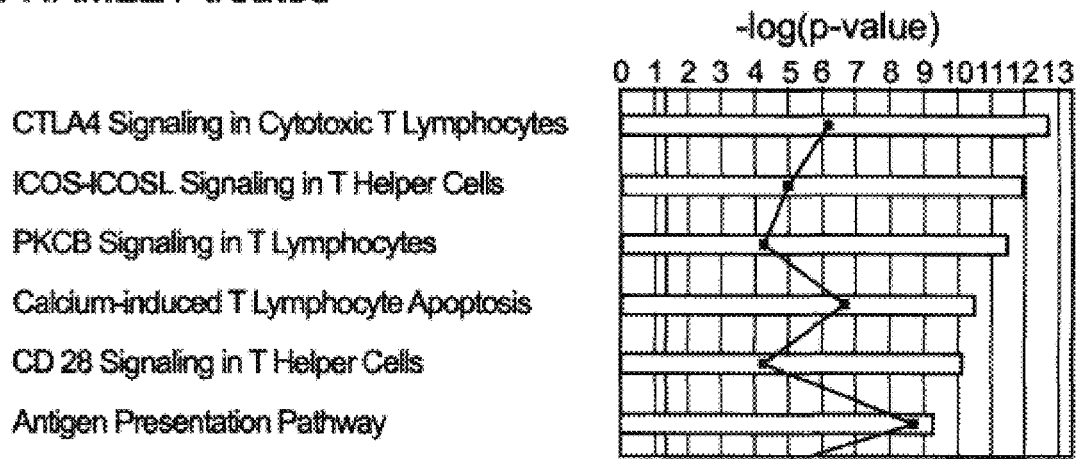
FIG. 9. Pathways enriched in control compared to HAMLET-treated samples (A) Ingenuity Pathway Analysis of genes enriched in sham treated mice compared to HAMLET-treated suggested increased activity of immunity pathways. (B) In vitro transcriptomic response in DLD-1 cells. To identify pathways altered by HAMLET-treatment, Signaling Pathway Impact Analysis (SPIA) was employed. A two-dimensional where the X-axis shows the overrepresentation evidence while the Y-axis shows the perturbation evidence. (C) Top five pathways impacted by HAMLET-treatment showed an activation of Protein processing in the ER and Cytokine-receptor interaction and inhibition of two general cancer pathways as well as inactivation of HTLV-I infection-pathway.

In mock treated mice, GSEA detected increased expression of genes relevant for acquired immunity and specifically for T-cells, including CD96, CD3γ in the TCR complex and KLRD1 in the killer cell lectin like receptor-dependent pathway (FIG. 9). Ingenuity analysis confirmed the higher expression of specific immunity genes in untreated tumors and a selected number of gene sets were very highly enriched (FDR q-val<0.0001 and FWER p-val<0.001), highly enriched genes included CD96 in the MHC II complex, the conserved receptor CD3G and KLRD1. Highly scoring pathways included CTLA4 cytotoxic T cell signaling, ICOS signaling in T helper cells, $Ca^{2+}$-induced T lymphocyte apoptosis as well as T helper cell and antigen presentation pathways and IL-4 signaling.

Effects of HAMLET on Colon Cancer Cells, In Vitro

Figure 4A:
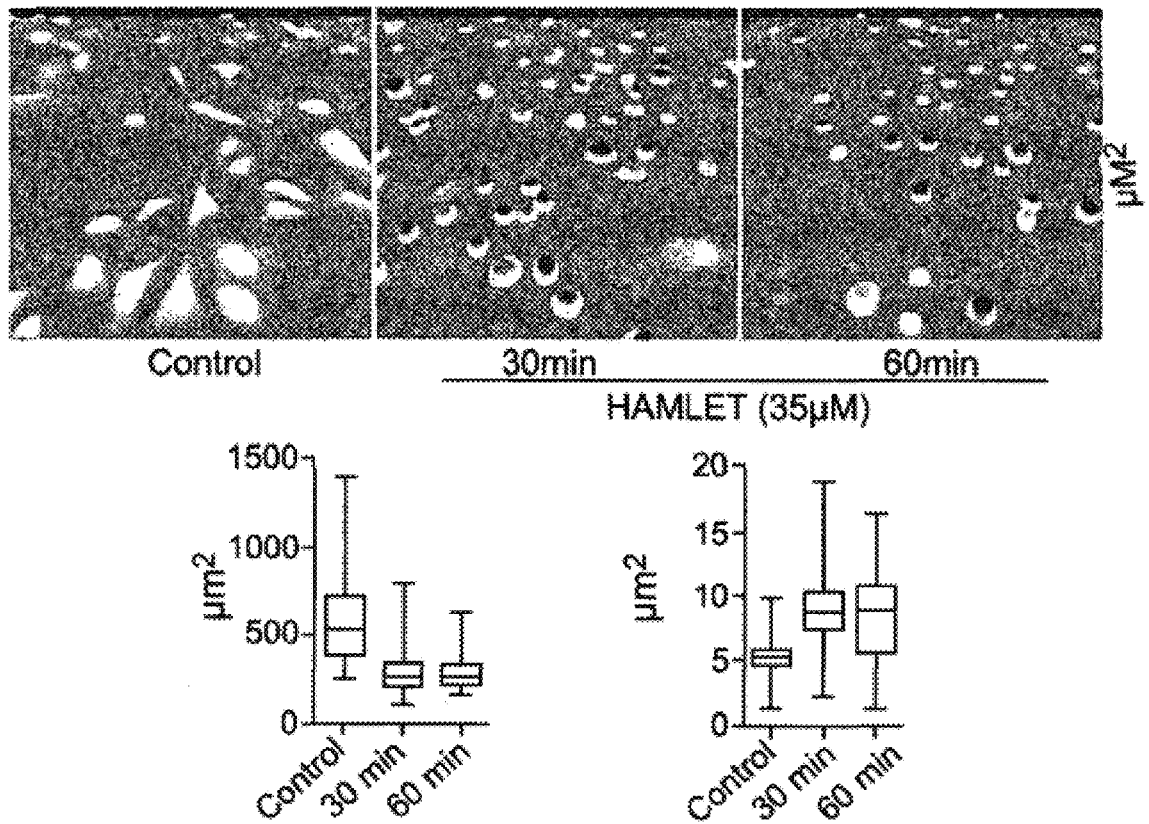
FIG. 4A-H. Effects of HAMLET on WNT/β-catenin pathway proteins in vitro.
Figure 4B:
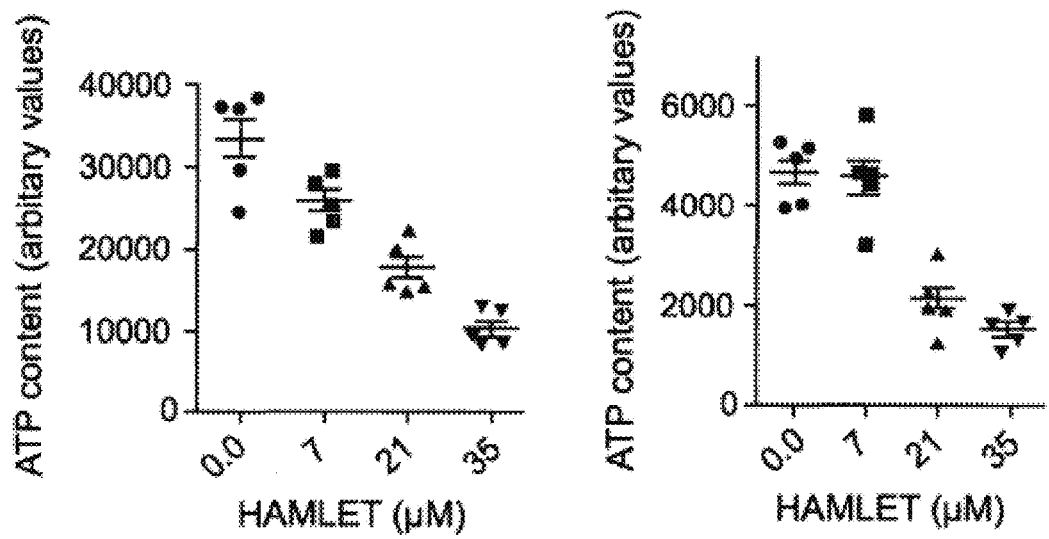
Figure 4C:
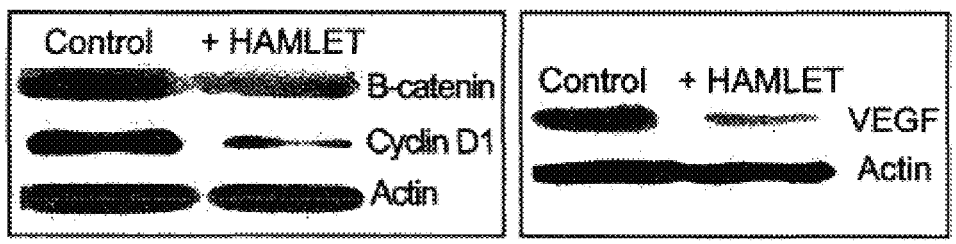

To better understand direct, short-term effects of HAMLET as opposed to more long-term effects on tissues surviving HAMLET treatment, we used the human colon cancer cell line DLD1, carrying homozygous inactivating mutations of the APC tumor suppressor (Ilyas M, et al. (1997) Proc Natl Acad Sci USA 94: 10330-10334). First, the susceptibility of the DLD1 cells to HAMLET was determined by morphological assessment, using real-time holographic imaging. HAMLET caused cellular rounding up in a time dependent manner and a decrease in cell area (p<0.0001 compared to control, FIG. 4A). In parallel, there was an increase in maximum thickness (p<0.001). HAMLET caused a reduction in cell adherence (FIG. 4A), compatible with initiation of detachment and cell death. A dose and time-dependent loss of viability was observed by quantifications of ATP levels and PrestoBlue (FIG. 4B).

Figure 4D:
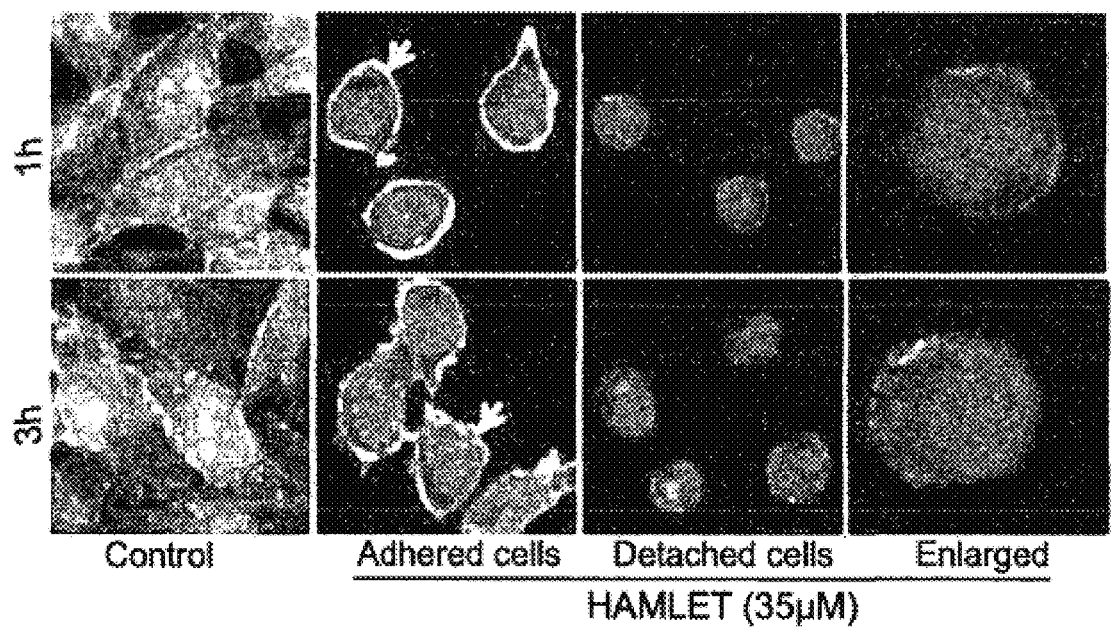
Figure 4D:
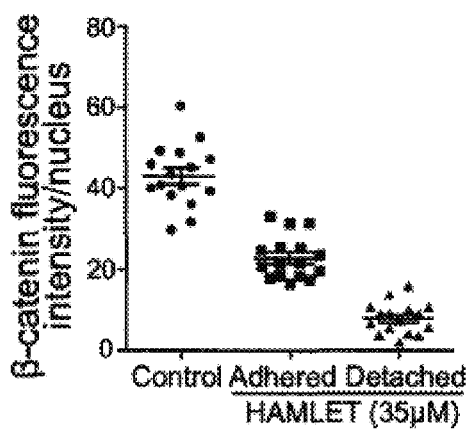
Figure 4E:
Figure 4F:
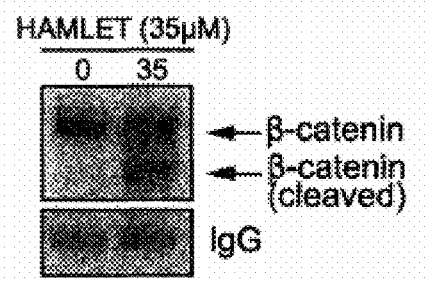
Figure 4G:
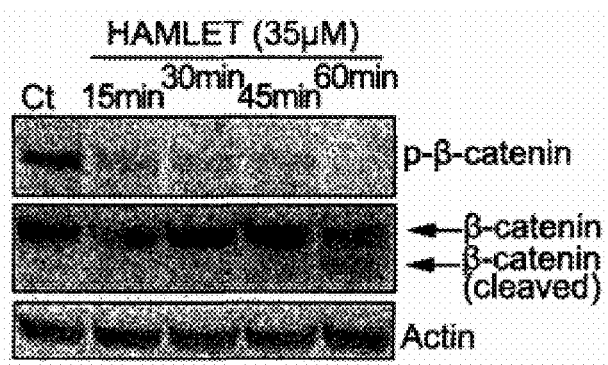
Figure 4H:
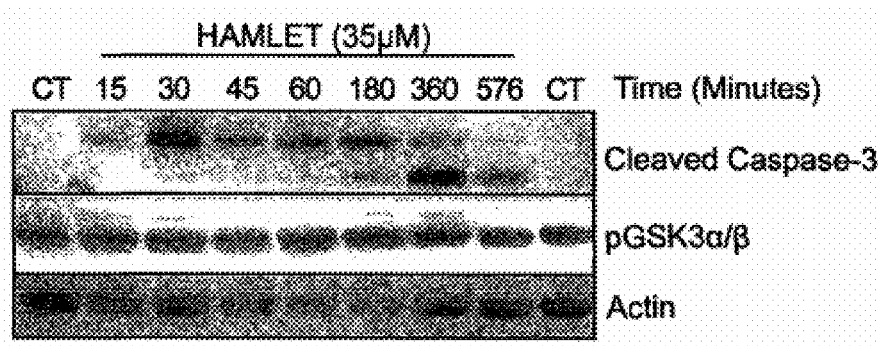

The effect of HAMLET on β-catenin expression was examined by confocal microscopy on fixed cells, stained with β-catenin-specific antibodies. HAMLET caused a rapid change in β-catenin distribution. In control cells, staining was diffuse throughout the cytoplasm and nuclei but after HAMLET exposure, nuclear β-catenin staining was lost and cytoplasmic staining was reduced. In parallel, β-catenin was accumulating at the cytoplasmic membrane (FIG. 4D). By Western blot analysis, time and dose dependent β-catenin fragmentation (110 and 80 kDa) was detected in HAMLET treated DLD1 cells (FIG. 4E, F, G). Previously, β-catenin fragmentation has been shown to be caspase dependent. HAMLET activation of caspase-3 was detected in DLD1 cells (FIG. 4H), confirming effector caspase-activation by HAMLET in tumor cells. To address the role of caspases for HAMLET induced β-catenin fragmentation, the pan-caspase inhibitor zVAD was used, with the cystein protease inhibitor leupeptin as a control (FIG. 5A). zVAD inhibited β-catenin fragmentation in response to HAMLET, but leupeptine had no effect. The loss of nuclear β-catenin staining in response to HAMLET was partially reversed by zVAD, in about 20% of the cells, but not in the remaining cells. HAMLET also reduced β-catenin phosphorylation (FIG. 4G), in a time-dependent manner. GSK3α/β phosphorylates b-catenin for proteasomal degradation. GSK3α/β activation by HAMLET was excluded, as no change in GSK3α/β phosphorylation was detected by western blots (FIG. 4H), indicating that HAMLET is not modulating the Wnt pathway by this mechanism.

Figure 5A:
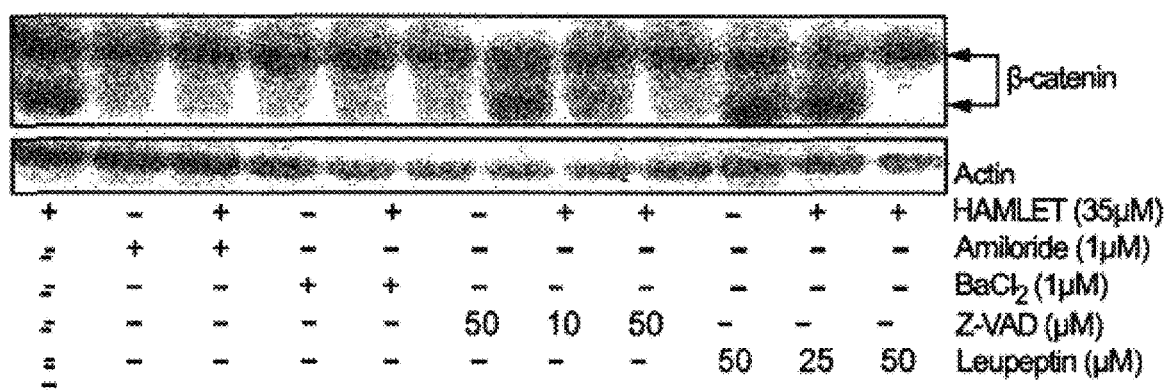
FIG. 5A-C. Ion channel-dependent degradation and nuclear translocation of β-catenin.
Figure 5B:
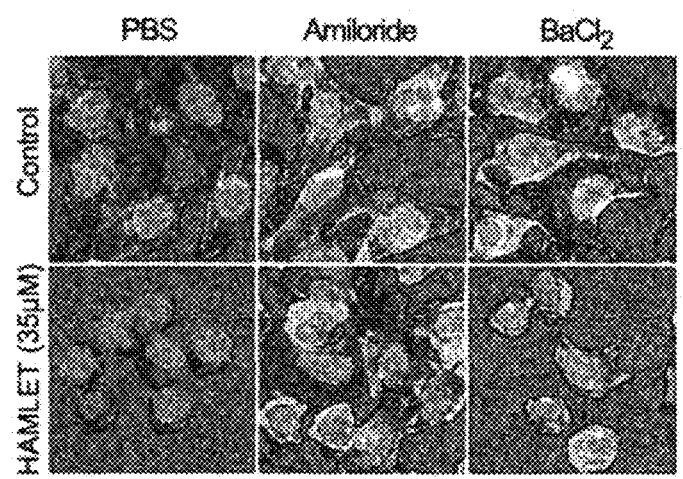

Ion channels have been found to support oncogenic transformation and tumors in $APC^{Min/+}$ mice show increased expression of amiloride-sensitive epithelial $Na^+$ channels (ENaC). HAMLET has recently been shown to activate specific ion fluxes across tumor cell membranes and such fluxes explain many aspects of the cell death response (Storm et al., Manuscript). To address if ion fluxes are involved in HAMLET's effects on β-catenin homeostasis, tumor cells were pretreated with the ion channel inhibitors Amiloride and Barium chloride. By confocal microscopy, these inhibitors were shown to reverse the HAMLET-induced reduction in nuclear β-catenin levels (FIG. 5B). Furthermore, the ion channel inhibitors blocked both β-catenin fragmentation and caspase-3 activation (FIG. 5A).

Figure 5C:
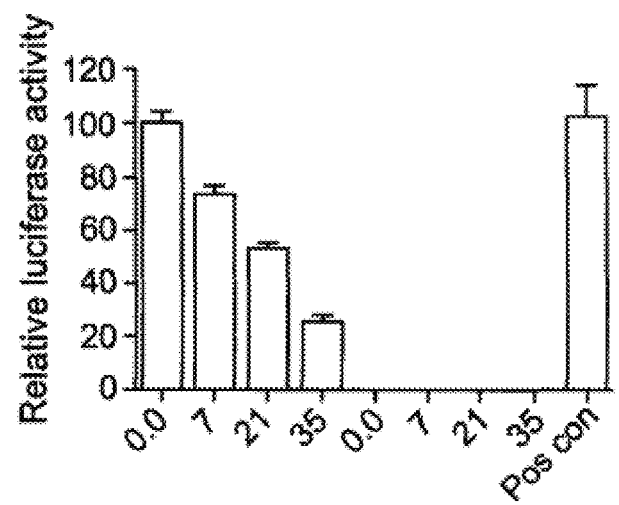
Figure 6A:
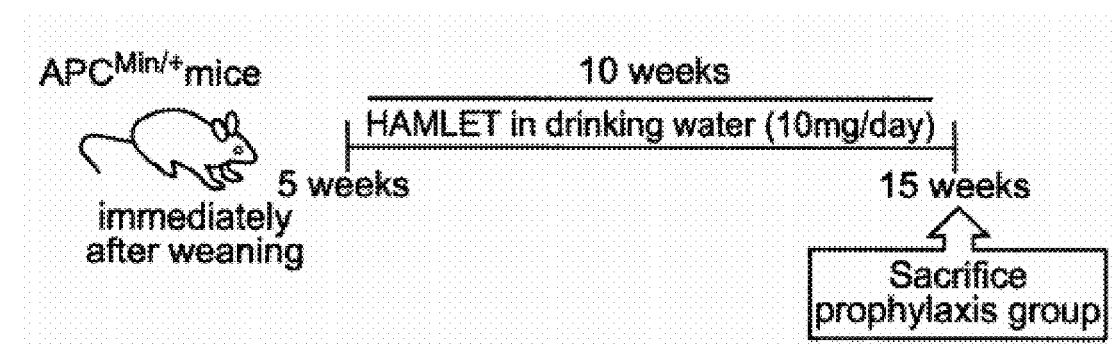
FIG. 6A-E. HAMLET prophylaxis reduces intestinal tumor development. $APC^{min}$ mice were provided with 10 mg/day of HAMLET in the drinking water for 10 weeks and sacrificed at 15 weeks of age.
Figure 6B:
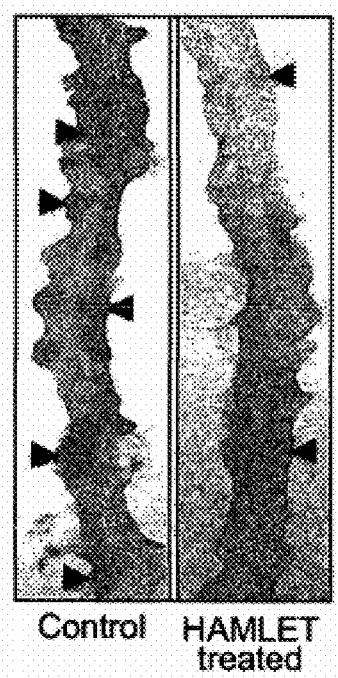
Figure 6C:
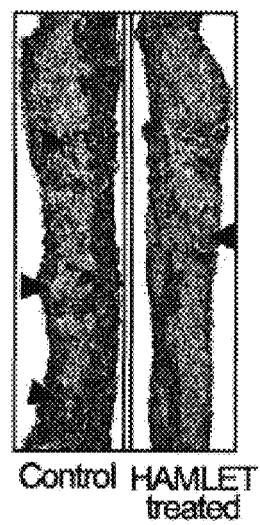
Figure 6D:
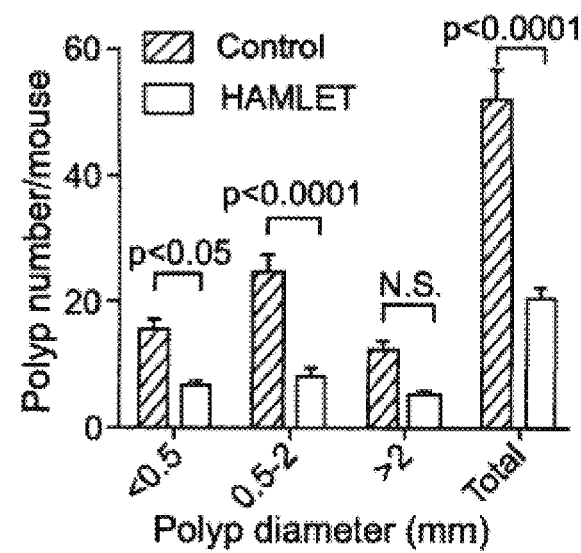
Figure 6E:
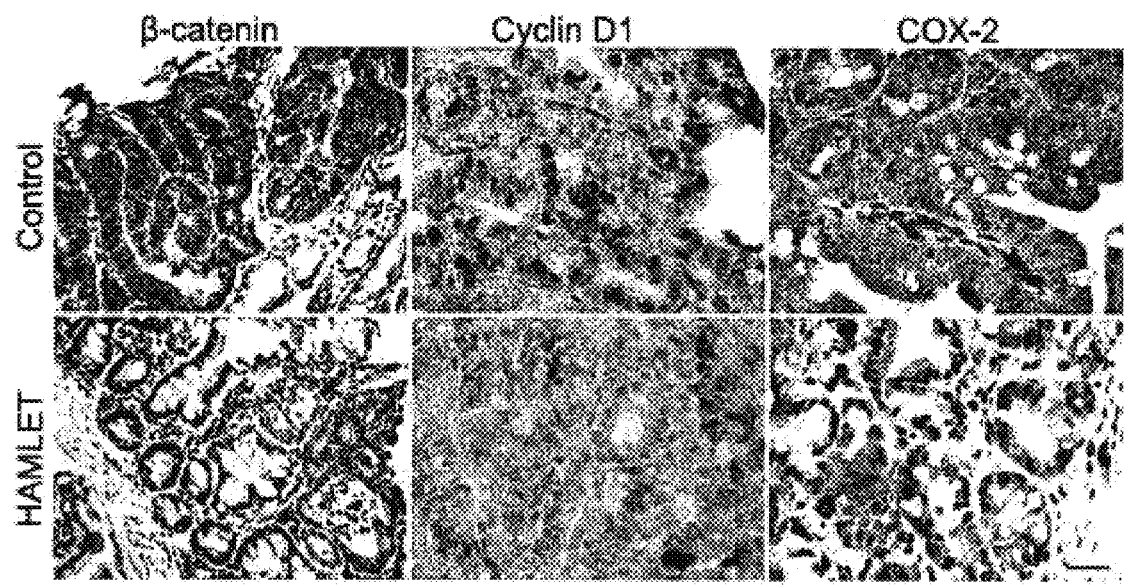

The cyclin D1 and VEGF protein levels were reduced in tissue biopsies from HAMLET treated mice, suggesting that β-catenin dependent gene expression might be affected. The TOP-flash dual luciferase reporter assay was used to quantify β-catenin-dependent promoter activity in HAMLET treated versus control cells. A dose dependent reduction in luciferase activity was detected after 3 hours of HAMLET treatment (FIG. 5C).

These finding show that β-catenin integrity and activity is altered in HAMLET treated colon cancer cells. This effect was mediated by ion channels, which triggered caspase-3-dependent β-catenin fragmentation as well as cell death pathways, consistent with the in vivo changes in β-catenin and related proteins.

HAMLET Acts as a Prophylactic Agent Against Colon Cancer

To address if peroral HAMLET administration may prevent tumor formation, $APC^{Min/+}$ mice were provided with HAMLET in the drinking water (10 mg/ml) from the time of weaning until week 17. Controls received drinking water alone. A marked reduction in tumor development was observed (FIG. 1A-F). Quantification of polyps in intestinal segments opened longitudinally showed a reduction in polyp number in the HAMLET treated group (FIG. 1B, p<0.01). A reduction in size was also evident in methylene blue stained sections of intestinal segments (FIG. 1C). H&E staining of "swiss roll" sections of the intestinal segments confirmed these differences compared to control mice, as fewer and smaller tumors were observed (FIG. 1D).

These results show that in addition to its therapeutic effects, HAMLET prevents colon cancer development in genetically susceptible mice.

EXAMPLE 2

Tumoricidal Activity Test from Crude Milk Extract Mixed with Oleate

A crude extract of human breast milk was obtained using the following treatments
1. Defatting milk by centrifugation
2. Removal of most milk proteins by ammonium sulfate precipitation (264 g/L or ~50% of a saturated solution) at 4° C., overnight.
3. Collect soluble extract by centrifugation 120 mg of sodium oleate was added into 10 ml of milk extract. It was calculated that this represented 100 times the molar excess of the protein present. This calculation was carried out using the protein content of the human breast milk extract as listed in Constituents of human milk, United Nations University Centre which are set out in the following table.

| Protein | g/100 ml |
| --- | --- |
| Total | 1.1 |
| Casein 0.4 | 0.3 |
| α-lactalbumin | 0.3 |
| Lactoferrin | 0.2 |
| IgA | 0.1 |
| IgG | 0.001 |
| Lysozyme | 0.05 |
| Serum albumin | 0.05 |
| β-lactoglobulin | — |

It was assumed that the total amount of protein present in the human milk extract used (minus the casein which is removed during the ammonium sulphate precipitation)

$$= \alpha\text{-lactalbumin} + \text{lactoferrin} + \text{lysozyme} + \text{serum albumin} + \beta\text{-lactoglobulin}$$

$$= 0.3 + 0.2 + 0.05 + 0.05 = \sim 0.7 \text{ g}/100 \text{ ml} = \sim 7 \text{ g/L}$$

Other possible protein-oleate complexation that could occur during the mixture steps. Lysozyme+oleate (protein:lipid=1:11-48)(K. Wilhelm, et al. (2009) FEBS J., 276, 3975-3989) Serum albumin+oleate (protein:lipid=1:6) (Zunszain P. A. et al. (2003) BMC Struct. Biol. 3, 6) b-lactoglobulin+oleate (protein:lipid=1:7.5-10)(Kamila Liskova, et al. (2011) Eur. J. Lipid Sci. Technol. 113, 1207-1218)
Lactoferrin (Unknown)

Assuming 5× excess of oleate is needed to form active complex with a-lactalbumin, ~70× molar excess of oleate is needed to complex with all these proteins. The molar concentration of total protein in the milk extract was estimated to be ~400 µM (using MW=14.2 kDa). To account for the deviation in the amount of different milk proteins and also that complexation is based on diffusion process in the solution, 100× molar excess of oleate was used. The pH of the mixture was lowered to pH 2 with 1M hydrochloric acid. Whilst not being bound by theory, it is possible that the low pH releases the $Ca^{2+}$ ions present in proteins such as α-lactalbumin present in the crude milk extract, unfolds the protein and exposes the hydrophobic patches for binding to the oleate ions. This means that structural alteration of α-lactalbumin is not accompanied by addition of extra elements, e.g. EDTA, that may make the composition unsuitable for pharmaceutical or nutraceutical use.

The mixture was heated at 50° C. for 30 minutes and then dialyzed against phosphate-buffered saline (1:100) for 2 hours and double dialyzed against water (1:100), overnight. The dialyzed samples were lyophilized and used for activity testing.

Activity Testing

Activity of the milk-oleate mixture was tested on colon carcinoma cells (DLD1) by measurement of ATP level and by using PrestoBlue cell viability assay. Briefly, 100000 cells/well were plated overnight in 96-well plate. The cells were washed twice with PBS and incubated with respective samples for 3 hours and 24 hours on separate plates. 5% Fetal calf serum (FCS) was added after 1 hour of incubation. ATP levels and Prestoblue cell viability measurement were done according to manufacturer's instructions.

Figure 10A:
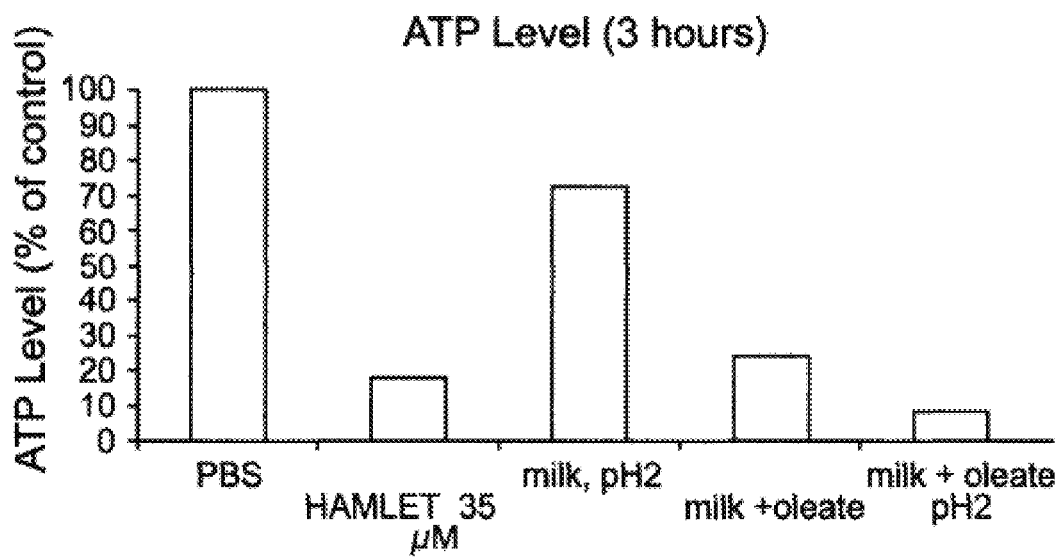
FIG. 10A-B is a graph showing the activity of a composition of the second aspect of the invention when tested on colon carcinoma cells (DLD1) using a cell viability assay that measures ATP level at (FIG. 10A) 3 hours and (FIG. 10B) 24 hours.
Figure 10B:
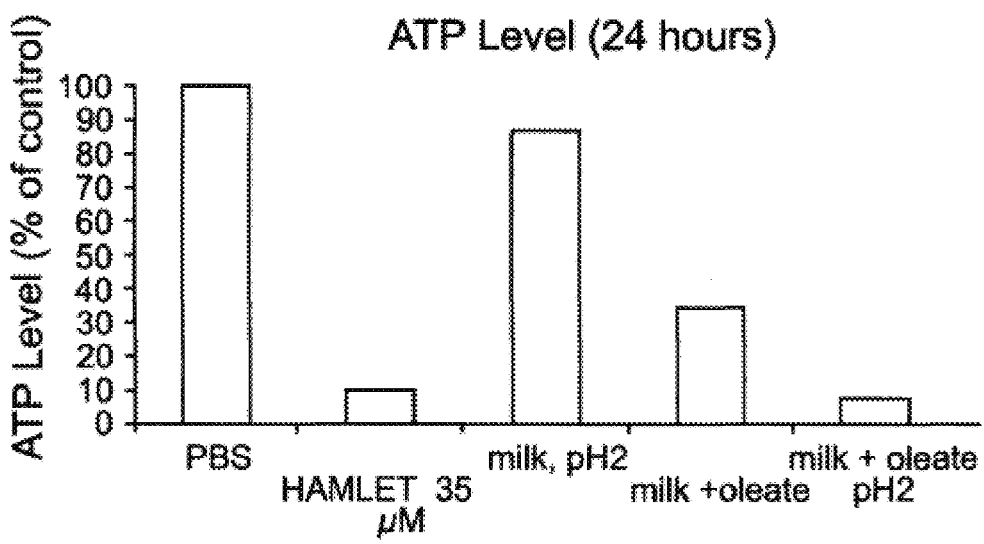
Figure 11:
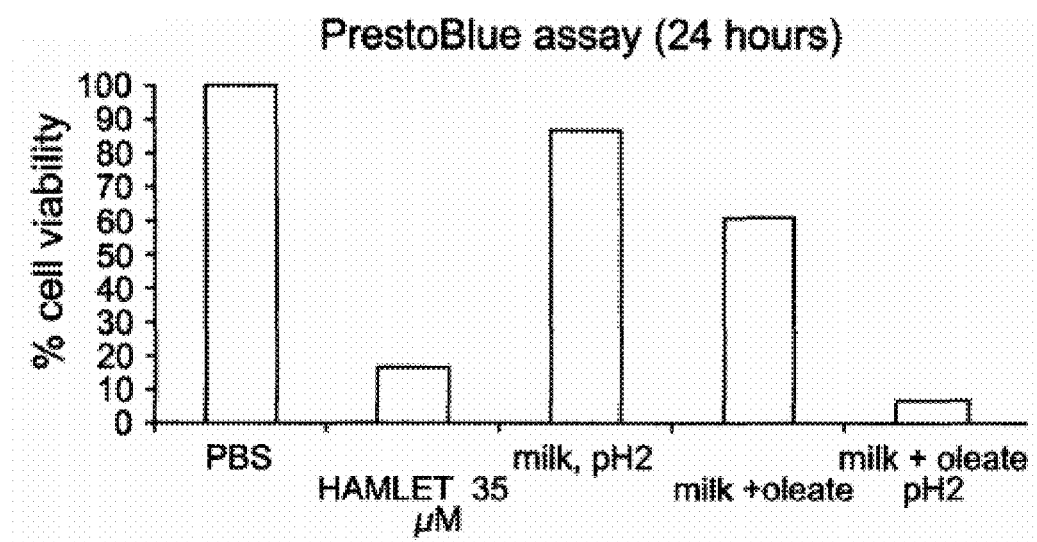
FIG. 11 is a graph showing the activity of a composition of the second aspect of invention when tested on colon carcinoma cells (DLD1) using PrestoBlue cell viability assay.
Figure 12A:
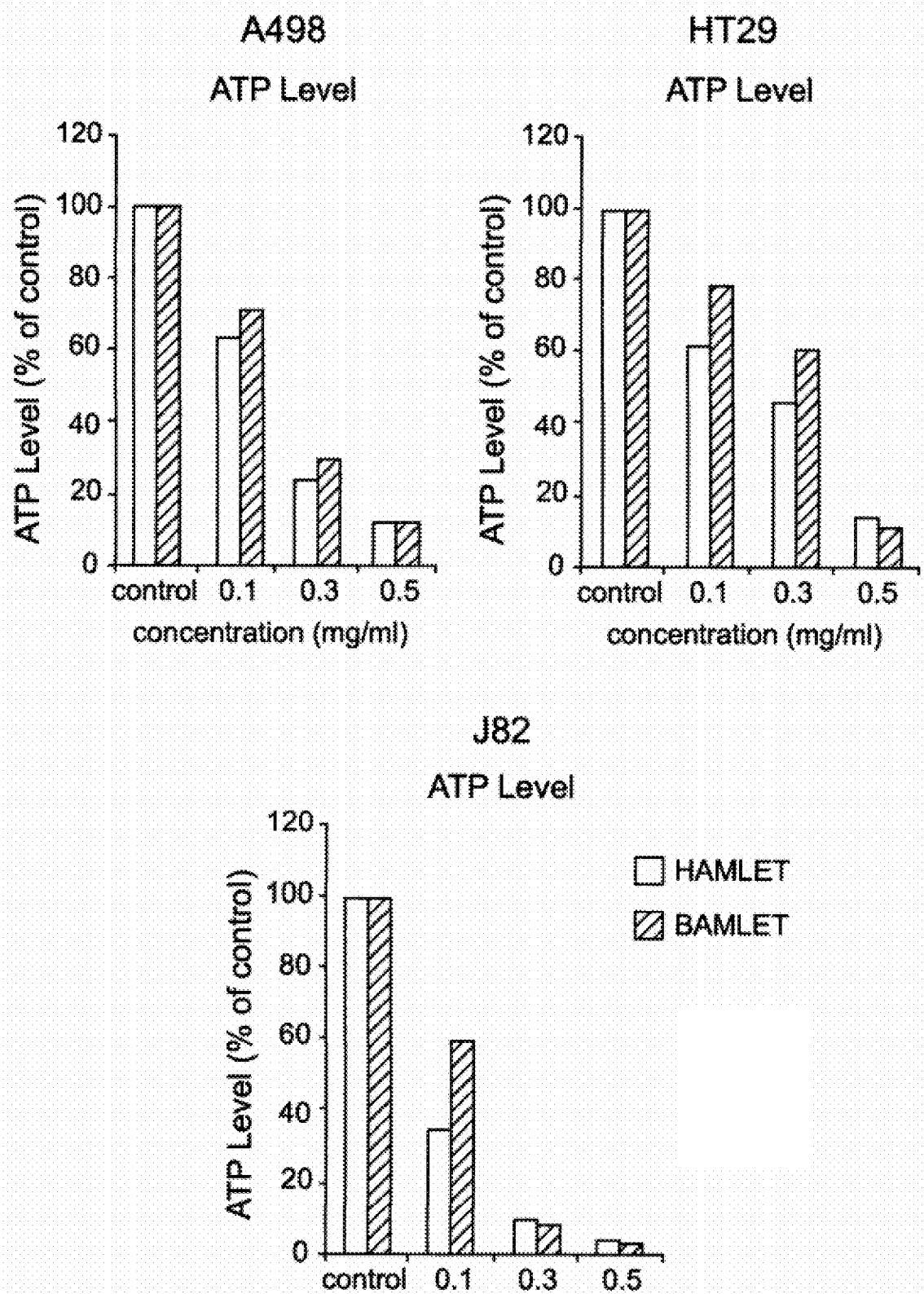
FIG. 12A-B presents graphs showing a comparison of the cellular activity of complexes of the first aspect of the invention derived from human alphalactalbumin (HAMLET) and bovine alphalactalbumin (BAMLET) when tested on a range of carcinoma cells using a cell viability assay that measures ATP level at 3 hours (FIG. 12A) and also using PrestoBlue cell viability assay (FIG. 12B).
Figure 12B:
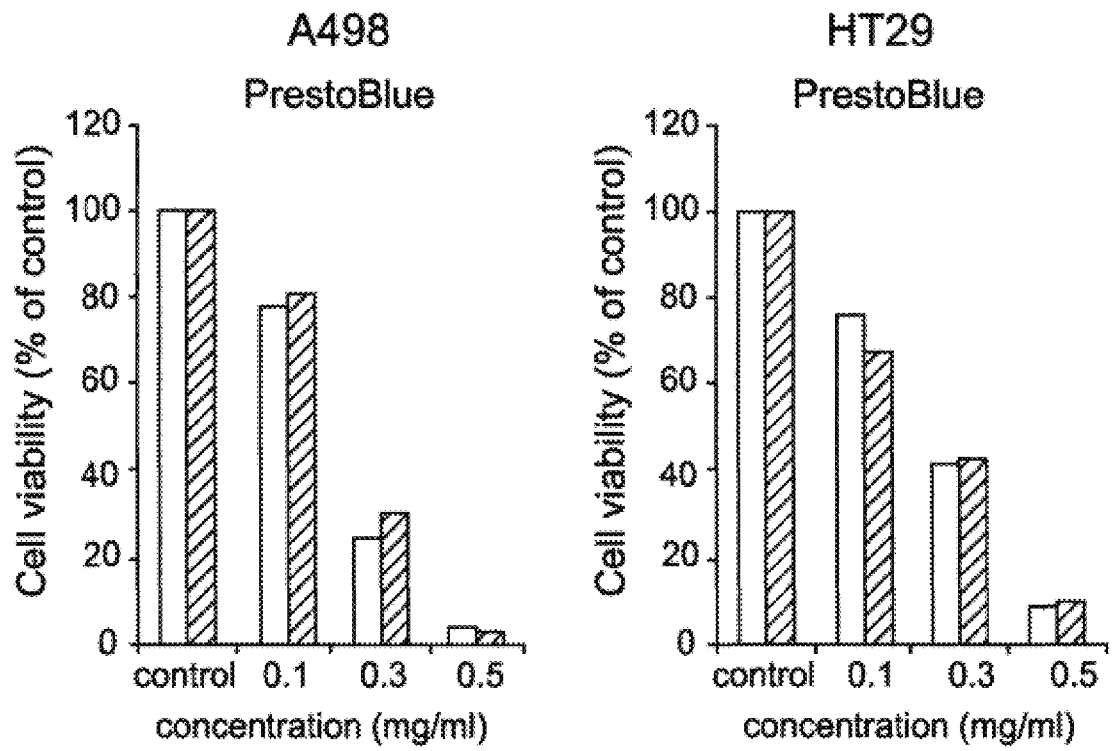
Figure 12B:
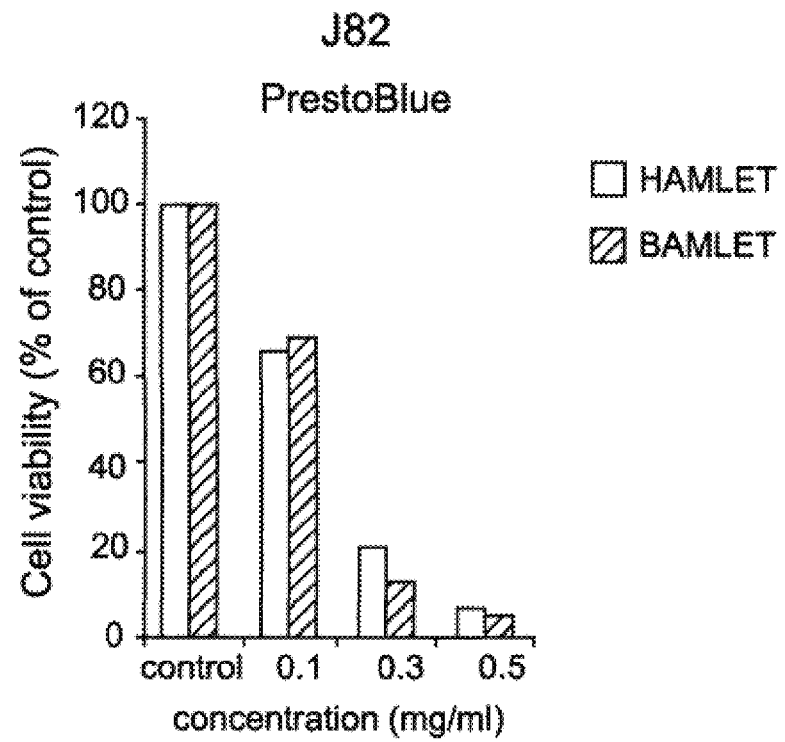
Figure 13A:
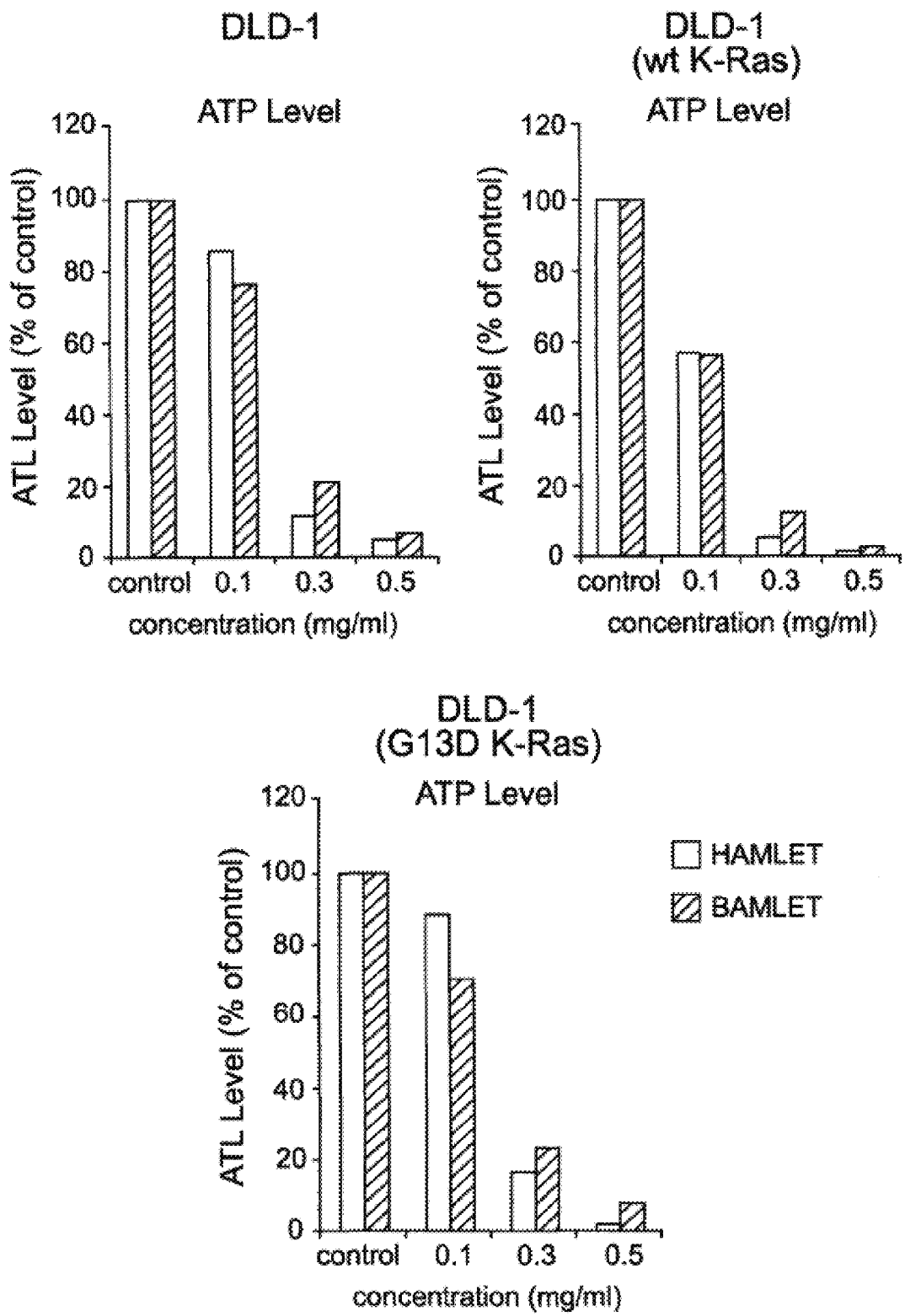
FIG. 13A-B presents graphs showing a comparison of the cellular activity of complexes derived from human alphalactalbumin (HAMLET) and bovine alphalactalbumin (BAMLET) when tested on a range of carcinoma cells using a cell viability assay that measures ATP level at 3 hours (FIG. 13A) and also using PrestoBlue cell viability assay (FIG. 13B).
Figure 13B:
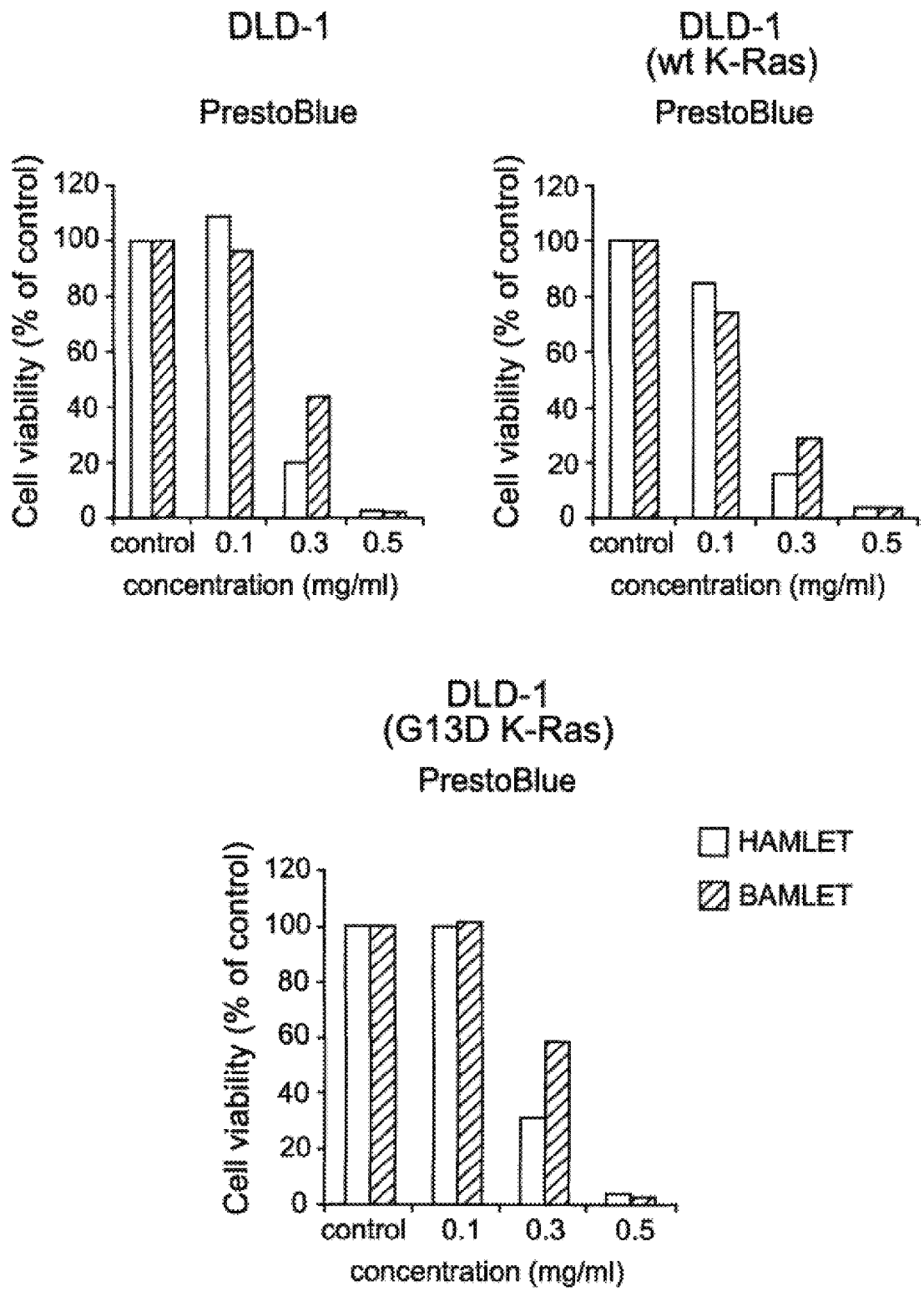
Figure 14:
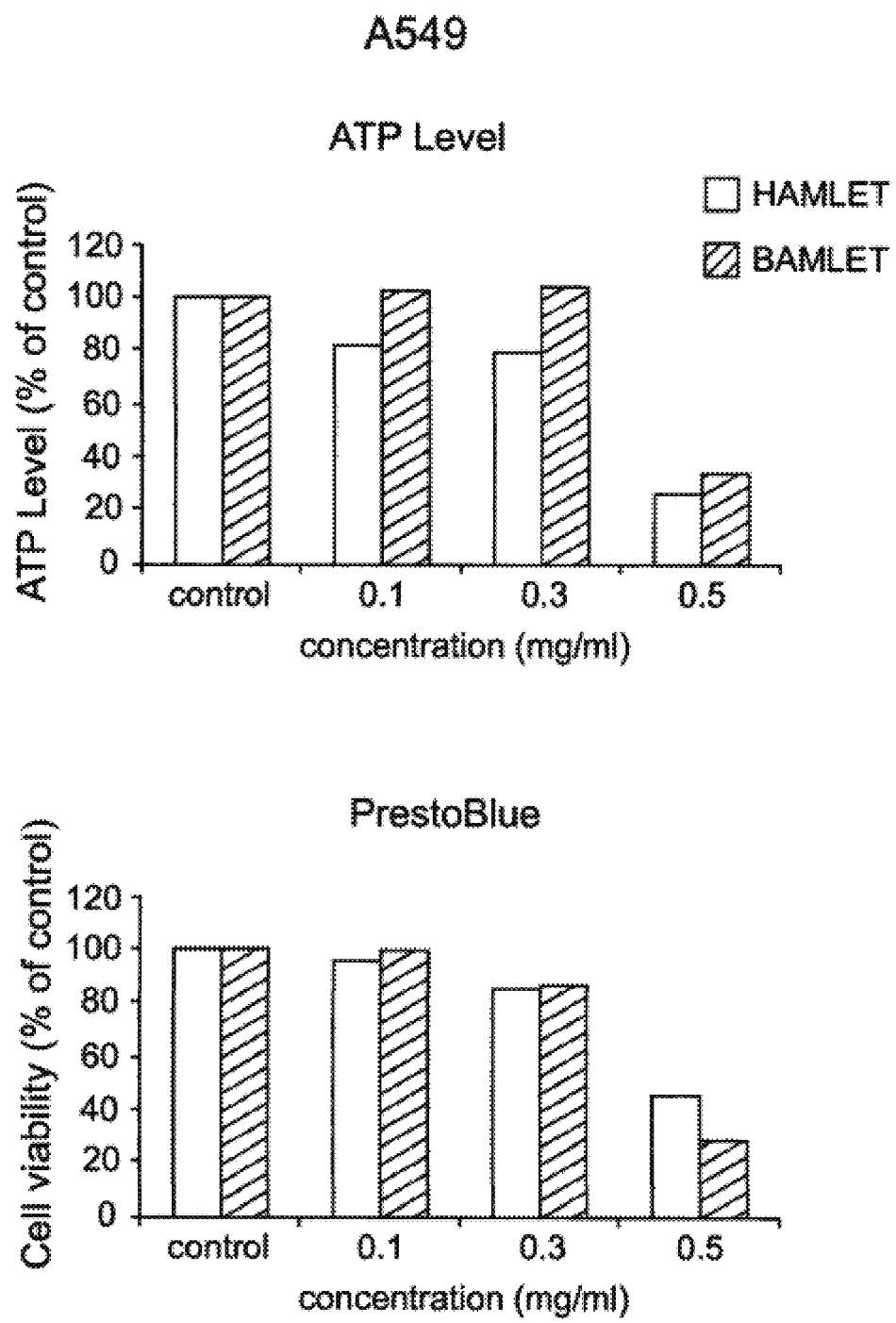
FIG. 14 presents graphs showing a comparison of the cellular activity of complexes of the first aspect of the invention derived from human alphalactalbumin (HAMLET) and bovine alphalactalbumin (BAMLET) when tested on A540 carcinoma cells using a cell viability assay that measures ATP level at 3 hours and also using PrestoBlue cell viability assay.

The ATP results at 3 and 24 hours are shown in attached FIG. 10A-B and the Prestoblue results are shown in FIG. 11. These results show that:

Milk, pH 2: The milk extract, acidified to pH 2, without oleate, did not show high level of tumoricidal activity.

Milk+oleate: The milk extract, mixed with oleate, without acidification, was not as efficient as HAMLET.

Milk+oleate, pH 2: The milk extract, acidified to pH 2 and mixed with oleate, showed comparable tumoricidal activity as that by HAMLET. Thus, this is the active material.

**Estimated Yield by Using this Milk+Oleate Mixing Method

We obtained ~160 mg of lyophilized materials from 10 ml of milk extract. For the above cell viability test, 22.3 mg of lyophilized material (milk extract, acidified to pH 2 and mixed with oleate) was dissolved in 555 µl of PBS to make up a 40 mg/ml stock solution. 5 µl of this stock solution was added to the cells.

Translating this volume in the perspective of HAMLET; with 10 ml of milk extract, we could obtain 160 mg of powder. This would give us 160 mg/(40 mg/ml)=4 ml of active solution, which is equivalent to 4 ml of 10 mg/ml of HAMLET or 40 mg of HAMLET from 10 ml of milk. Translating this amount back to the crude α-lactalbumin amount in human breast milk, it is almost equal to a 100% conversion efficiency. If this is the case, then the method represents an extremely effective method for preparing HAMLET. However, it is also possible that other complexes had also been formed that were contributing to the activity. It is also clear that other components of the composition are not interfering with the activity but may in fact be enhancing it.

EXAMPLE 3

Comparison of Effects of HAMLET and BAMLET on Tumour Cells

An experiment was run to confirm that BAMLET produced generally similar results to HAMLET in particular in relation to a range of tumour cells.

HAMLET and BAMLET was produced using a method similar to that described in WO2010/131237. In summary 350 μM human or bovine alpha-lactalbumin (Davisco) was mixed with 3.5 mM sodium oleate (protein:lipid ratio, 1:10) and the mixture incubated at 55° C. for 10 min. The mixture was then allowed to equilibrate to room temperature for 20 min.

Various concentrations (0.1, 0.3 and 0.5 mg/ml) of BAMLET and HAMLET were tested side-by-side for activity on a range of tumour cells using the method described in Example 2. The cells used included A498 (Kidney cancer cells), HT29 (colorectal cancer cells), J82 (bladder cancer cells), DLD-1 and variants (colorectal cancer cells) and A549 (lung cancer cells). The results of the ATP level and PrestoBlue tests are shown in FIGS. 12A-B, 13A-B, and 14. These show that, as compared to a control, both HAMLET and BAMLET produced a concentration dependent reduction in tumour cell viability and thus produce qualitatively similar effects biologically.

In addition, as discussed above, it has been reported that HAMLET activates ion fluxes in tumour cells and that this is a factor contributing to the activity (Storm et al., Plos one (2013), 8, 3, e58578). A comparison was made of the effects of HAMLET and BAMLET on the ion channels. Using the methodology described in Storm et al. (2013 supra) potassium, calcium and sodium fluxes were measured. To examine if HAMLET modulates ion channel activity in tumor cells, we first quantified changes in intracellular $Ca^{2+}$ and $K^+$. Lung carcinoma cells were first preloaded with the Fluo-4 $Ca^{2+}$ fluorophore Fluo-, exposed to HAMLET, BAMLET (both at 35 aM) or a PBS control and examined by real time confocal microscopy for changes in fluorescence intensity.

Both HAMLET and BAMLET triggered a rapid, stepwise increase in intracellular $Ca^{2+}$ (FIG. 15), but with considerable heterogeneity.

With regard to the potassium channel activation, the FluxOR™ potassium ($K^+$) channel assay was performed on the TECAN infinite F200 (Tecan Group, Switzerland), according to the manufacturer's instructions (Invitrogen). Briefly, this involved FluxOR™ loading buffer (Hank's Balanced Saline Solution, (HBSS) buffered with 20 mM HEPES and pH adjusted to 7.4 with NaOH. Powerload™ concentrate and water-soluble Probenecid were used respectively to enhance the dye solubility and retention, respectively. Media were removed from the cell plates manually, and 80 μL of loading buffer containing the FluxOR™ dye mix was applied to each well. Once inside the cell, the nonfluorescent AM ester form of the FluxOR™ dye is cleaved by endogenous esterases into a thallium-sensitive indicator. The dye was loaded for 60 minutes at room temperature and then removed with the supernatent. After washing with dye-free PBS buffer, a final volume of 80 μL assay buffer containing water-soluble probenecid was added.

Figure 15:
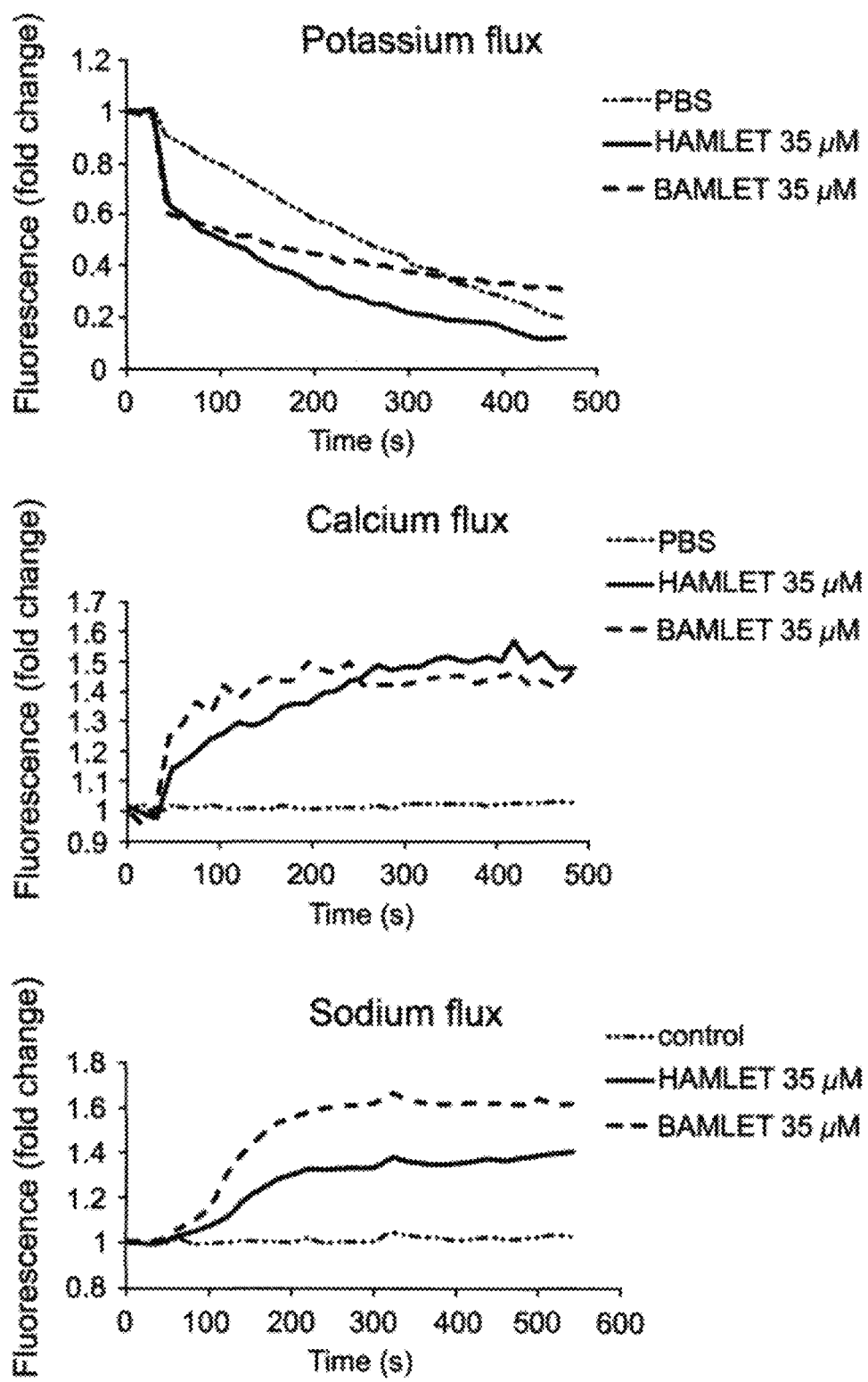
FIG. 15 shows the results of potassium calcium, and sodium flux experiments carried out using HAMLET and BAMLET.

As shown in in FIG. 15, both HAMLET and BAMLET showed similar significant activation effects in the potassium channel assay.

In addition, sodium influx in Jurkat cells was measured by using CoroNa Green Sodium indicator. The fluorescence was quantified every 20-second interval for a 10-minute total measurement period. Both HAMLET and BAMLET triggered an increase of fluorescence signal when added to the cells while the PBS control did not (FIG. 15).

The results, especially the prolonged $Ca^{2+}$ response and the magnitude of IC' channel activation, suggest that ion channel activation by HAMLET distinguishes carcinoma cells from healthy, differentiated cells.

It is clear, that effects on ion channels are similar when either HAMLET or BAMLET were used. This leads to the conclusion that BAMLET would produce similar effects to HAMLET in the method of the first aspect of the invention.

---

The invention claimed is:

1. A method for preventing formation of a colon cancer, wherein the method comprises administering to an individual that does not have colon cancer, a biologically active complex comprising:
   (i) alpha-lactalbumin;
   (ii) a variant of alpha-lactalbumin, wherein the variant comprises an alpha-domain and has at least 80% sequence identity to alpha-lactalbumin; or
   (iii) a peptide of up to 50 amino acids and comprising an alpha-domain of alpha-lactalbumin; and
   (iv) a fatty acid or a salt thereof.

2. The method of claim 1 wherein the fatty acid is oleic acid or a salt thereof.

3. The method of claim 1, wherein the alpha-lactalbumin has the sequence of human or bovine alpha-lactalbumin.

4. The method of claim 1, wherein the individual has a genetic predisposition to colon cancer, and the genetic predisposition is a mutation in the adenomatous polyposis coli (APC) gene.

5. The method of claim 4, wherein the mutation is a truncation of the APC gene.

6. The method of claim 1, wherein the alpha-lactalbumin is human alpha-lactalbumin and the biologically active complex is HAMLET, or the alpha-lactalbumin is bovine alpha-lactalbumin and the biologically active complex is BAMLET.

7. The method of claim 1, wherein the peptide is derived from the alpha domain of alpha-lactalbumin.

8. The method of claim 1, wherein the peptide comprises SEQ ID NO: 3 or 5.

9. The method of claim 1, wherein the variant of alpha-lactalbumin comprises the sequence of native mature alpha-lactalbumin wherein all of the cysteines have been mutated to other amino acids.

10. A method for preventing formation of a colon cancer, wherein the method comprises administering to an individual that does not have colon cancer a biologically active complex comprising alpha-lactalbumin or a variant thereof or a peptide of up to 50 amino acids comprising SEQ ID NO: 3 or 5 and a fatty acid or a salt thereof, wherein:
   i) the alpha-lactalbumin is human alpha-lactalbumin and the biologically active complex is HAMLET; or
   ii) the alpha-lactalbumin is bovine alpha-lactalbumin and the biologically active complex is BAMLET; and
   iii) the variant is a variant of native mature alpha-lactalbumin wherein all of the cysteines have been mutated to other amino acids.

11. A method for preventing formation of colon cancer, wherein the method comprises administering to an individual that does not have colon cancer a biologically active complex comprising:
   i) alpha-lactalbumin; or
   ii) a variant of alpha-lactalbumin, wherein the variant comprises an alpha domain and has at least 80% sequence identity to alpha-lactalbumin; and
   iii) a fatty acid or a salt thereof.

* * * * *

SEQUENCE LISTING

```
<160> NUMBER OF SEQ ID NOS: 6

<210> SEQ ID NO 1
<211> LENGTH: 123
<212> TYPE: PRT
<213> ORGANISM: Artificial Sequence
<220> FEATURE:
<223> OTHER INFORMATION: Recombinant Protein

<400> SEQUENCE: 1

Lys Gln Phe Thr Lys Ala Glu Leu Ser Gln Leu Leu Lys Asp Ile Asp
1               5                   10                  15

Gly Tyr Gly Gly Ile Ala Leu Pro Glu Leu Ile Ala Thr Met Phe His
            20                  25                  30

Thr Ser Gly Tyr Asp Thr Gln Ala Ile Val Glu Asn Asn Glu Ser Thr
        35                  40                  45

Glu Tyr Gly Leu Phe Gln Ile Ser Asn Lys Leu Trp Ala Lys Ser Ser
    50                  55                  60

Gln Val Pro Gln Ser Arg Asn Ile Ala Asp Ile Ser Ala Asp Lys Phe
65                  70                  75                  80

Leu Asp Asp Asp Ile Thr Asp Asp Ile Met Ala Ala Lys Lys Ile Leu
                85                  90                  95
```

Asp Ile Lys Gly Ile Asp Tyr Trp Leu Ala His Lys Ala Leu Ala Thr
            100                 105                 110

Glu Lys Leu Glu Gln Trp Leu Ala Glu Lys Leu
        115                 120

<210> SEQ ID NO 2
<211> LENGTH: 124
<212> TYPE: PRT
<213> ORGANISM: Artificial Sequence
<220> FEATURE:
<223> OTHER INFORMATION: Recombinant Protein

<400> SEQUENCE: 2

Met Lys Gln Phe Thr Lys Ala Glu Leu Ser Gln Leu Leu Lys Asp Ile
1               5                   10                  15

Asp Gly Tyr Gly Gly Ile Ala Leu Pro Glu Leu Ile Ala Thr Met Phe
            20                  25                  30

His Thr Ser Gly Tyr Asp Thr Gln Ala Ile Val Glu Asn Asn Glu Ser
        35                  40                  45

Thr Glu Tyr Gly Leu Phe Gln Ile Ser Asn Lys Leu Trp Ala Lys Ser
    50                  55                  60

Ser Gln Val Pro Gln Ser Arg Asn Ile Ala Asp Ile Ser Ala Asp Lys
65                  70                  75                  80

Phe Leu Asp Asp Asp Ile Thr Asp Asp Ile Met Ala Ala Lys Lys Ile
                85                  90                  95

Leu Asp Ile Lys Gly Ile Asp Tyr Trp Leu Ala His Lys Ala Leu Ala
            100                 105                 110

Thr Glu Lys Leu Glu Gln Trp Leu Ala Glu Lys Leu
        115                 120

<210> SEQ ID NO 3
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 6
<223> OTHER INFORMATION: Xaa is an amino acid other than cysteine
<220> FEATURE:
<221> NAME/KEY: VARIANT
<222> LOCATION: 28
<223> OTHER INFORMATION: Xaa is an amino acid other than cysteine

<400> SEQUENCE: 3

Lys Gln Phe Thr Lys Xaa Glu Leu Ser Gln Leu Leu Lys Asp Ile Asp
1               5                   10                  15

Gly Tyr Gly Gly Ile Ala Leu Pro Glu Leu Ile Xaa Thr Met Phe His
            20                  25                  30

Thr Ser Gly Tyr Asp Thr Gln Ala
        35                  40

<210> SEQ ID NO 4
<211> LENGTH: 43
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 11
<223> OTHER INFORMATION: Xaa is an amino acid other than cysteine

```
<220> FEATURE:
<221> NAME/KEY: VARIANT
<222> LOCATION: 31
<223> OTHER INFORMATION: Xaa is an amino acid other than cysteine
<220> FEATURE:
<221> NAME/KEY: VARIANT
<222> LOCATION: 40
<223> OTHER INFORMATION: Xaa is an amino acid other than cysteine

<400> SEQUENCE: 4

Leu Asp Asp Asp Ile Thr Asp Asp Ile Met Xaa Ala Lys Lys Ile Leu
1               5                   10                  15

Asp Ile Lys Gly Ile Asp Tyr Trp Leu Ala His Lys Ala Leu Xaa Thr
            20                  25                  30

Glu Lys Leu Glu Gln Trp Leu Xaa Glu Lys Leu
        35                  40

<210> SEQ ID NO 5
<211> LENGTH: 40
<212> TYPE: PRT
<213> ORGANISM: Artificial Sequence
<220> FEATURE:
<223> OTHER INFORMATION: Synthetic peptide

<400> SEQUENCE: 5

Lys Gln Phe Thr Lys Ala Glu Leu Ser Gln Leu Leu Lys Asp Ile Asp
1               5                   10                  15

Gly Tyr Gly Gly Ile Ala Leu Pro Glu Leu Ile Ala Thr Met Phe His
            20                  25                  30

Thr Ser Gly Tyr Asp Thr Gln Ala
        35                  40

<210> SEQ ID NO 6
<211> LENGTH: 43
<212> TYPE: PRT
<213> ORGANISM: Artificial Sequence
<220> FEATURE:
<223> OTHER INFORMATION: Synthetic peptide

<400> SEQUENCE: 6

Leu Asp Asp Asp Ile Thr Asp Asp Ile Met Ala Ala Lys Lys Ile Leu
1               5                   10                  15

Asp Ile Lys Gly Ile Asp Tyr Trp Leu Ala His Lys Ala Leu Ala Thr
            20                  25                  30

Glu Lys Leu Glu Gln Trp Leu Ala Glu Lys Leu
        35                  40
```